US012751604B2

(12) United States Patent
Yeh et al.

(10) Patent No.: US 12,751,604 B2
(45) Date of Patent: Oct. 6, 2026

(54) ROTARY KNOB ASSEMBLY FOR A STEERABLE MEDICAL DEVICE

(71) Applicant: EndoVista, Inc., Chicago, IL (US)

(72) Inventors: Yun-Siung Tony Yeh, Vernon Hills, IL (US); Tahua Yang, Chicago, IL (US); David G. Matsuura, Solana Beach, CA (US); Belinko K. Matsuura, Encitas, CA (US); Philip J. Simpson, Escondido, CA (US)

(73) Assignee: EndoVista, Inc., Chicago, IL (US)

( * ) Notice: Subject to any disclaimer, the term of this patent is extended or adjusted under 35 U.S.C. 154(b) by 504 days.

(21) Appl. No.: 18/172,051

(22) Filed: Feb. 21, 2023

(65) Prior Publication Data

US 2023/0200632 A1 Jun. 29, 2023

Related U.S. Application Data

(63) Continuation of application No. PCT/IB2021/061881, filed on Dec. 16, 2021.

(Continued)

(51) Int. Cl.

*A61B 1/00* (2006.01)
*A61B 1/005* (2006.01)
*A61M 25/01* (2006.01)

(52) U.S. Cl.

CPC ........ *A61B 1/0052* (2013.01); *A61B 1/00042* (2022.02); *A61B 1/00147* (2013.01); *A61B 1/0057* (2013.01); *A61M 25/0133* (2013.01)

(58) Field of Classification Search

CPC . A61B 1/0052; A61B 1/00042; A61B 1/0057; A61B 1/00135; A61B 1/00134;

(Continued)

(56) References Cited

U.S. PATENT DOCUMENTS 5,921,917 A 7/1999 Barthel et al.
6,458,142 B1 10/2002 Faller et al.

(Continued)

FOREIGN PATENT DOCUMENTS

EP 1197240 B1 2/2006
EP 2319388 B1 10/2015

(Continued)

OTHER PUBLICATIONS

Supplemental European Search Report for European Application No. 2192892 dated Oct. 28, 2024, 59 pages.

(Continued)

*Primary Examiner* — Anh Tuan T Nguyen
*Assistant Examiner* — Rynae E Boler
(74) *Attorney, Agent, or Firm* — Jordan IP Law, LLC

(57) ABSTRACT

A control device for use with a steerable medical device comprises a steering shaft rotatable about a longitudinal axis thereof, a first steering cam is affixed to the steering shaft to rotate in unison therewith. A second steering cam is mounted on the steering shaft and freely rotatable about the longitudinal axis of the steering shaft independent of the steering shaft. A latch assembly is operatively connected to the first steering cam and the second steering cam and operable in an inactive configuration in which the first and second steering cams are positioned to maintain first and second steering wires in an un-tensioned or reduced tension state, and further operable in an active configuration in which the first and second steering cams are positioned to maintain the first and second steering wires in a tensioned state. A rotary knob assembly is also disclosed.

13 Claims, 17 Drawing Sheets

Related U.S. Application Data

(60) Provisional application No. 63/200,426, filed on Mar. 5, 2021.

(58) Field of Classification Search
CPC .......... A61M 25/0133; A61M 25/0136; A61M 25/0147
See application file for complete search history.

(56) References Cited

U.S. PATENT DOCUMENTS

| | | | | |
|---|---|---|---|---|
| 7,771,416 | B2 | 8/2010 | Spivey et al. | |
| 8,257,386 | B2 | 9/2012 | Lee et al. | |
| 8,366,607 | B2 | 2/2013 | Sullivan et al. | |
| 8,591,405 | B2 | 11/2013 | Hoshino | |
| 8,608,649 | B2 | 12/2013 | McWeeney et al. | |
| 8,777,898 | B2 | 7/2014 | Suon et al. | |
| 8,808,167 | B2 | 8/2014 | Hoshino | |
| 8,808,169 | B2 | 8/2014 | Macnamara et al. | |
| 8,961,401 | B2 | 2/2015 | Takeucki et al. | |
| 9,241,612 | B2 | 1/2016 | Hoshino | |
| 9,931,024 | B2 | 4/2018 | Hatano | |
| 10,149,605 | B2 | 12/2018 | Petersen et al. | |
| 10,576,243 | B2 | 3/2020 | Suon et al. | |
| 11,678,792 | B2 * | 6/2023 | Attinger | A61B 1/0055 138/110 |
| 2006/0069311 | A1 | 3/2006 | Sullivan et al. | |
| 2009/0062606 | A1 | 3/2009 | Ueda et al. | |
| 2011/0295068 | A1 * | 12/2011 | Petersen | A61B 1/05 600/131 |
| 2015/0112139 | A1 * | 4/2015 | Fujitani | A61B 1/00066 600/117 |
| 2015/0164524 | A1 * | 6/2015 | Malkowski | A61B 34/71 606/205 |
| 2015/0305596 | A1 | 10/2015 | Oskin et al. | |
| 2018/0117280 | A1 * | 5/2018 | Chu | A61B 1/0051 |
| 2019/0038113 | A1 * | 2/2019 | Chu | A61B 1/00133 |
| 2019/0110661 | A1 * | 4/2019 | Do | A61B 1/0057 |
| 2019/0117937 | A1 * | 4/2019 | Humphrey | A61B 1/0052 |
| 2019/0350440 | A1 | 11/2019 | Leong et al. | |

FOREIGN PATENT DOCUMENTS

| | | | |
|---|---|---|---|
| EP | 3544482 | A1 | 10/2019 |
| EP | 3598932 | A2 | 1/2020 |
| JP | H11258522 | A | 9/1999 |
| JP | 2000152910 | A | 6/2000 |
| JP | 2004073606 | A | 3/2004 |
| JP | 2005124632 | A | 5/2005 |
| JP | 2007330280 | A | 12/2007 |
| JP | 2015208548 | A | 11/2015 |
| WO | 2013106444 | A1 | 7/2013 |
| WO | 2018162559 | A1 | 9/2018 |
| WO | 2020089893 | A2 | 5/2020 |

OTHER PUBLICATIONS

Translation of Notification for Reasons of Rejection for Japanese Application No. 2023-546171 dated Jul. 26, 2024, 6 pages.
Translation of Office Action for Taiwanese Application No. 110147560 dated Sep. 22, 2022.

* cited by examiner

ROTARY KNOB ASSEMBLY FOR A STEERABLE MEDICAL DEVICE

FIELD

The present disclosure generally concerns steerable medical devices such as endoscopes and, more particularly, to a control device and/or rotary knob assembly for use with such steerable medical devices.

BACKGROUND

Steerable medical devices and other minimally invasive surgical tools are being increasingly used to perform medical procedures inside a patient's body. Steerable devices generally include an elongated shaft and one or more control wires having distal ends secured at or adjacent the distal articulation tip section of the shaft. One or more control knobs, levers or other mechanisms are provided to selectively tension the control wires in order to bend the device in a desired direction.

An example of a steerable medical device is an endoscope, which is a medical instrument used in endoscopic procedures to view patient's internal tissues or organs for diagnostic or therapeutic purpose. The basic design of most flexible endoscopes consist of a small diameter flexible elongated insertion tube with an articulation tip section, a video camera and a light source mounted at the distal tip, an internal working channel for suction, fluid irrigation, or passing small surgical instruments through, a handle with one or more tip articulation control knobs to control the direction of the distal tip, a suction on/off valve, and other control buttons for video image recording or image quality adjustment.

Most endoscopes are reusable instruments and thus have to be cleaned and disinfected after single patient use. Cleaning and disinfection of endoscopes requires a rigorous reprocessing consisting of multiple processing steps. Because of the intricate design of the endoscopes with narrow internal channels, assembled components and crevices, the instruments are very difficult to clean and disinfect consistently to an acceptable level despite the extensive reprocessing procedures. Indeed, studies have shown that endoscopes that underwent rigorous reprocessing steps are often still contaminated with organic residual matter, and the resulting potential transmission of microorganisms from contaminated endoscopes between patient uses poses a significant infection risk.

Various publications also disclose a reusable endoscope handle with a detachable, disposable flexible catheter. However, such reusable endoscope handles are often difficult to use in that the process for attaching and/or detaching the disposable flexible catheter is difficult to achieve or otherwise not intuitive. Furthermore, the design of a reusable handle combined with a detachable disposable catheter with an imaging unit is generally complex and has several product commercialization challenges such as the noted lack of ease of use; the ongoing need to clean and disinfect the reusable handle after each use; often low scope reliability; and unattainable low cost due to the presence of expensive (and potentially environmentally hazardous) components in the disposable portion.

Single use endoscopes, designed for disposal after a single patient use, are another approach to reduce infection risk to patients resulting from the use of contaminated endoscopes, and have been developed and used in endoscopic procedures for a number of years. The disposable components include not only the entire scope with the attached flexible catheter and the fluid flow conduits that are in direct contact with patient tissue or fluids, but also include those components that are not in direct patient contact such as the signal wire cable connected to the display and the printed circuit board with electronic components inside the handle. Such single use endoscopes are typically manufactured and assembled with the control wires suitably tensioned (to provide predictable deflection of the distal tip during end use) prior to sterilization processing, packaging and shipping. However, due to the tension force exerted by the wires, the articulation section of the distal tip after sterilization and storage can often be distorted due to heat and moisture encountered during sterilization, transportation and storage, which could affect the steerability of the endoscope. This issue is particularly significant with endoscopes having smaller articulation tube diameters. Further complicating matters, such single use endoscopes have to be packaged straight with the catheter inserted into a long protective tube to prevent it from forming a permanent bend after sterilization, transportation and storage. The large size of scope packaging results in higher packaging and transportation cost and also requires more product storage space at clinical institutions.

Some steerable medical devices are known to provide un-tensioned control wires prior to use. For example, U.S. Pat. No. 8,777,898 discloses a two-piece device comprising a reusable handle and attachable catheter. The attachable catheter includes un-tensioned control wires terminated at a proximal end by a catheter control member. The handle includes a handle control member complementary to the catheter control member. When the proximal end of the catheter is attached to the handle, the catheter and handle control members are coupled together such that the control wires are placed under tension. However, as noted, the device described in the '898 patent is a two-piece system and therefore suffers from the above-described shortcomings.

Thus, technologies that overcome the above-noted limitations and provide improved manufacturability, reliability and usability for steerable medical devices would represent a welcome advancement in the art.

SUMMARY

The above-noted shortcomings are addressed by the teachings of the instant disclosure. In particular, in a first embodiment, a control device for use with a steerable medical device comprises a first steering shaft rotatable about a longitudinal axis thereof. A first steering cam is affixed to the first steering shaft such that the first steering shaft rotates in unison with the first steering cam about the longitudinal axis of the first steering shaft. The first steering cam further comprises a first attachment portion for attachment of a first steering wire. A second steering cam is mounted on the first steering shaft and freely rotatable about the longitudinal axis of the first steering shaft independent of the first steering shaft. The second steering cam further comprises a second attachment portion for attachment of a second steering wire. A first latch assembly is operatively connected to the first steering cam and the second steering cam and is operable in an inactive configuration in which the first and second steering cams are positioned such that the first and second steering wires are maintained in an un-tensioned state, and is further operable in an active configuration in which the first and second steering cams are positioned such that the first and second steering wires are maintained in a tensioned state.

In the first embodiment, the first steering cam may comprise a first facing surface and the second steering cam comprise a second facing surface configured to be opposite the first facing surface. Further, the first latch assembly may further comprise at least one inactive notch and at least one active notch formed on the first facing surface, and at least one projection formed on the second facing surface. In the inactive configuration, alignment of the at least one projection with the at least one inactive notch positions the first and second steering cams such that the first and second steering wires are maintained in the un-tensioned state. On the other hand, in the active configuration, alignment of the at least one projection with the at least one active notch positions the first and second steering cams such that the first and second steering wires are maintained in a tensioned state. In this case, a biasing element, such as a spring deployed about the first steering shaft, may be provided to bias the second facing surface into contact with the first facing surface. A depth of the at least one inactive notch may be less than a depth of the at least one active notch. Further still, a slope of a first sidewall of the at least one inactive notch may be less than a slope of sidewalls of the at least one active notch.

In the first embodiment, a first user-controllable lever can be affixed to the first steering shaft such that the first steering shaft rotates in unison with the first lever.

The first embodiment may further include a second steering shaft rotatable about a longitudinal axis thereof, a third steering cam affixed to the second steering shaft such that the second steering shaft rotates in unison with the third steering cam about the longitudinal axis of the second steering shaft and a fourth steering cam mounted on the second steering shaft and freely rotatable about the longitudinal axis of the second steering shaft independent of the second steering shaft. In this case, the third steering cam may further comprise a third attachment portion for attachment of a third steering wire, and the fourth steering cam may further comprise a fourth attachment portion for attachment of a fourth steering wire. Further still, in this case, a second latch assembly is operatively connected to the third steering cam and the fourth steering cam, and is operable in the inactive configuration in which the third and fourth steering cams are positioned such that the third and fourth steering wires are maintained in the un-tensioned state, and is further operable in the active configuration in which the third and fourth steering cams are positioned such that the third and fourth steering wires are maintained in the tensioned state. A second user-controllable lever may be affixed to the second steering shaft such that the second steering shaft rotates in unison with the second lever.

A steerable medical device may comprise the control device of the first embodiment along with an insertion tube. By way of non-limiting example, such a steerable medical device may comprise an endoscope.

In a second embodiment, a steerable medical device may comprise a housing, an insertion tube and a rotary knob assembly rotatably mounted on and extending out of the housing and affixed to the insertion tube. In this embodiment, the rotary knob assembly comprises a bushing rotatably mounted on the housing and rotatably about a longitudinal axis of the housing and a user-controllable knob affixed to the bushing such that the bushing rotates in unison with the knob about the longitudinal axis. The knob assembly further includes an endotracheal tube retainer affixed to the knob such that the knob rotates in unison with the tube retainer, wherein the tube retainer is fabricated from an elastomer material. In an implementation, the bushing comprises a radially extending flange configured for engagement with an annular channel formed in the housing.

In the second embodiment, the housing and knob may respectively comprise at least one detent and at least one recess, or vice versa, configured for mutual engagement at least one defined-rotation position of the knob relative to the housing. Further, the housing may comprise a housing stop surface and the knob may comprise a knob stop surface, wherein the housing stop surface and the knob stop surface are configured to limit rotation of the knob when the housing stop surface contacts the knob stop surface. The housing stop surface and the knob stop surface may be configured to permit no more than 90° of rotation of the knob away from a zero-rotation position of the knob relative to the housing.

Further the second embodiment, the endotracheal tube retainer comprises a longitudinally-extending channel formed therein that defines a tube retainer sidewall that, in turn, has at least one longitudinally-extending slot formed therein. Additionally, the tube retainer sidewall may include at least one outer surface taper angle and, in a presently preferred embodiment, two outer surface taper angles that are different from each other.

One or more control devices of the first embodiment may be incorporated into a steerable medical device in accordance with the second embodiment. Similarly, a steerable medical device in accordance with the first embodiment may incorporate a rotary knob assembly in accordance with the second embodiment.

BRIEF DESCRIPTION OF THE DRAWINGS

The foregoing and other features and advantages will be discussed in detail in the following non-limiting description of specific embodiments in connection with the accompanying drawings, in which.

DETAILED DESCRIPTION OF THE PRESENT EMBODIMENTS

As used herein, phrases substantially similar to “at least one of A, B or C” are intended to be interpreted in the disjunctive, i.e., to require A or B or C or any combination thereof unless stated or implied by context otherwise. Further, phrases substantially similar to “at least one of A, B and C” are intended to be interpreted in the conjunctive, i.e., to require at least one of A, at least one of B and at least one of C unless stated or implied by context otherwise. Further still, the term “substantially” or similar words requiring subjective comparison are intended to mean “within manufacturing tolerances” unless stated or implied by context otherwise. Unless indicated otherwise, reference in this disclosure to absolute positional qualifiers, such as the terms “front,” “back,” “top,” “bottom,” “left,” “right,” etc., or to relative positional qualifiers, such as the terms “above,” “below,” “higher,” “lower,” “distal,” “proximal,” etc., or to qualifiers of orientation, such as “horizontal”, “vertical”, etc., is made to the orientation shown in the Figures.

Figure 1:
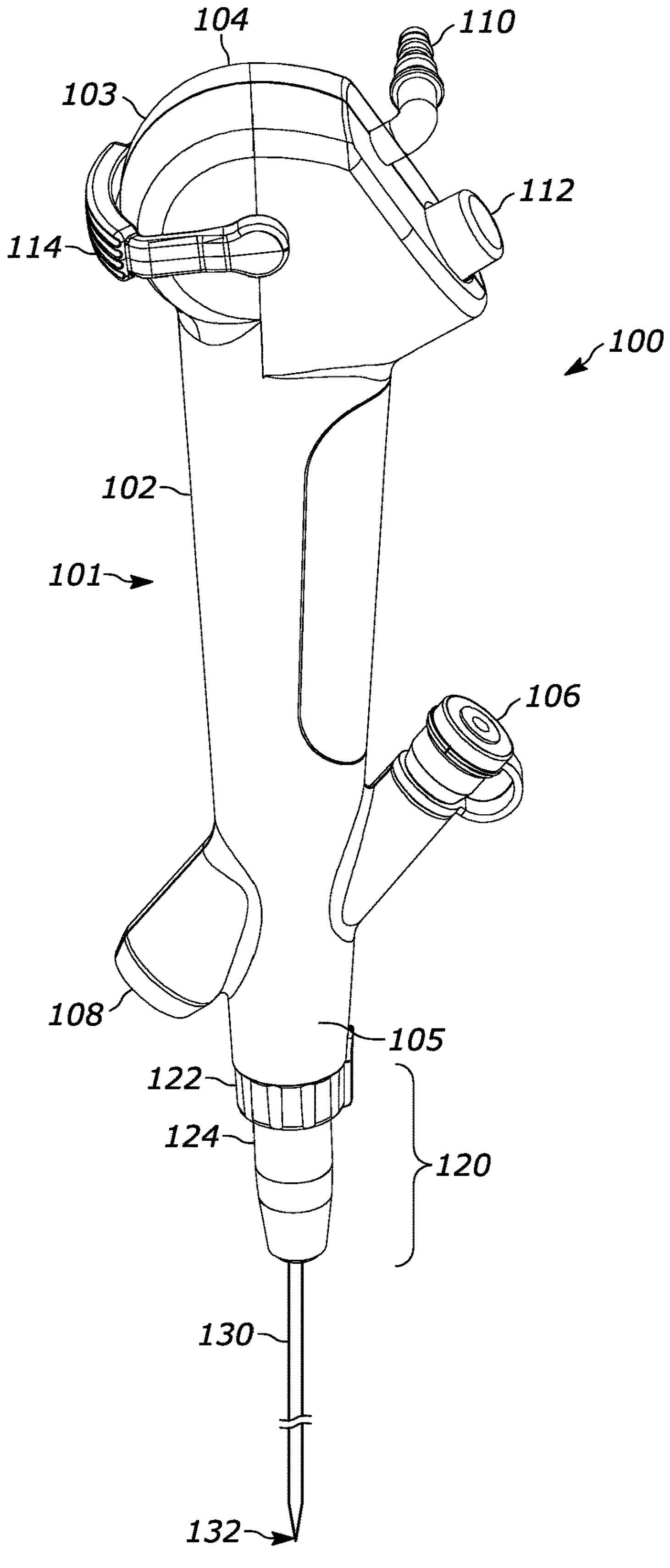
FIG. 1 illustrates a top, side elevation view of a steerable medical device, particularly an endoscope, in accordance with the instant disclosure.

Referring now to FIG. 1, a steerable medical device 100 in accordance with the instant disclosure is illustrated. In particular, the steerable medical device 100 shown in FIG. 1 is an endoscope in accordance with a presently preferred embodiment. However, it is understood that the steerable medical device 100 in accordance with the instant disclosure need not be limited to endoscopes and may comprise any of a number of similar such devices as will be known to those skilled in the art including, but not limited to, guiding catheters, imaging catheters, ablation catheters, and other steerable & deflectable catheters for diagnostic or therapeutic applications. As shown and described below, the steerable medical device 100 illustrated in FIG. 1 includes both a control device and rotary knob assembly in accordance with the instant disclosure. However, it is not required that the steerable medical device 100 comprise both the control device and rotary knob assembly described herein. That is, steerable medical devices in accordance with the instant disclosure may comprise one or more control devices, or a rotary knob assembly or both as dictated by design requirements.

As shown in FIG. 1, the steerable medical device 100 comprises a housing 101 formed from a first housing portion 102 and a second housing portion 104, where the housing 101 comprises a proximal end 103 and a distal end 105. Techniques for affixing or joining the first and second housing portions 102, 104 together to provide a unitary housing 101 are known to those skilled in the art. The housing 101 includes a biopsy valve 106 as well as a video port 108 disposed toward the distal end 105 of the housing 101. Toward the proximal end 103 of the housing 101, a suction port 110 and suction valve button 112 are provided. As shown, the suction port 110 is in the form of a swiveling, barbed elbow connector, and suction through the steerable medical device 100 is controlled through use of the suction valve button 112. A user-controllable lever 114 is provided at the proximal end 103 to actuate a control device as described in further detail below. Additionally, at the distal end 105, the steerable medical device 100 comprises a rotary steering assembly 120 that in turn comprises a user-controllable knob 122 and an endotracheal tube retainer 124 mounted on the user-controllable knob 122. As further illustrated, the steerable medical device 100 comprises a flexible insertion tube or catheter 130 extending out of the knob assembly 120 and terminating in a distal end 132 thereof. Though not shown in FIG. 1, the insertion tube 130 includes one or more control wires extending to an articulation section of the distal tip 132 to control actuation of the distal tip 132 in accordance with known techniques. Further, the insertion tube 130 may encompass other components depending on the nature of the steerable medical device 100. For example, in the case of an endoscope, as shown, the insertion tube 130 may enclose cabling to operate a light source and camera disposed at the distal end 132 of the insertion tube 130, as well as a small-diameter tube providing a working channel, also terminated in proximity to the distal end 132, coupled to both the biopsy port with the biopsy valve 106 and suction port 110 as described in greater detail below.

Figure 2:
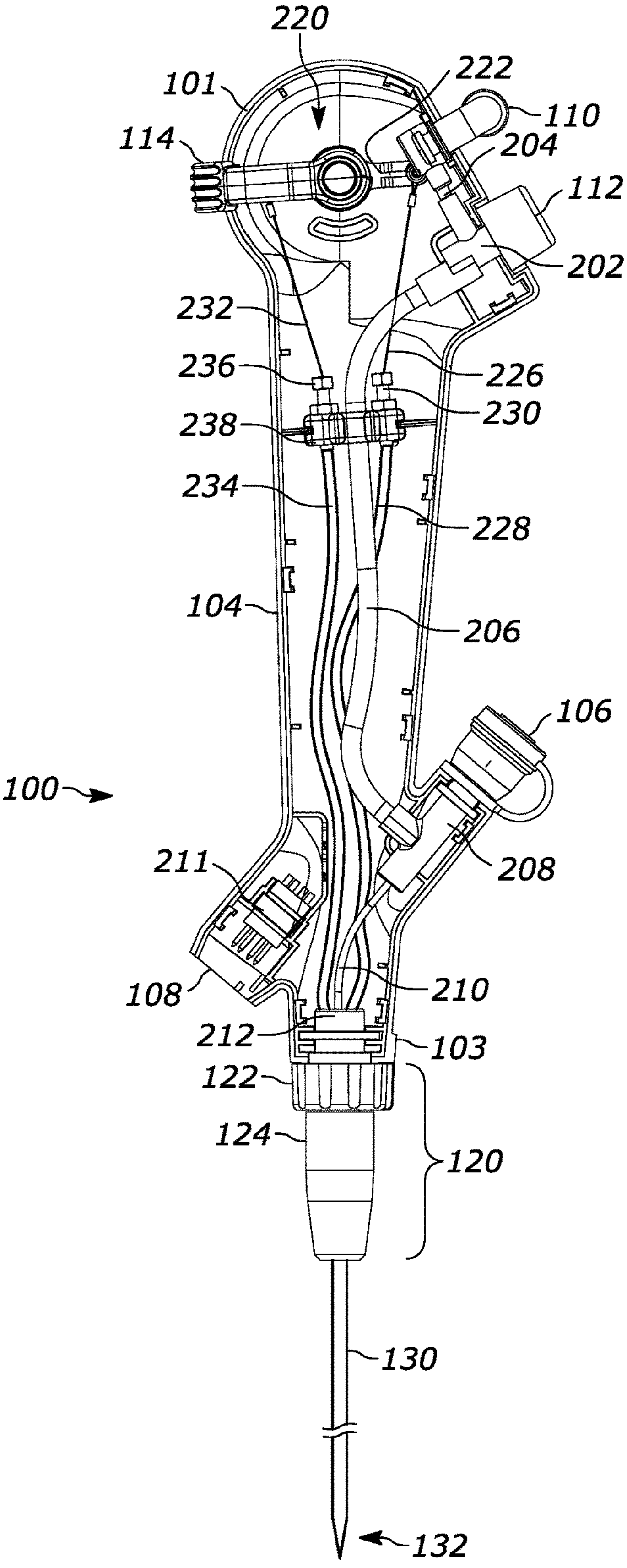
FIG. 2 is a side elevation view of the steerable medical device of FIG. 1 and in which a portion of a housing of the steerable medical device has been removed.

Referring now to FIG. 2, the first housing portion 102 has been removed, revealing the inner workings of the steerable medical device 100. In particular, the biopsy valve 106 comprises a working channel port 208 affixed to the housing 101 and providing access to a working channel tube 210 extending through the rotary knob assembly 120 toward the distal end 132 of the insertion tube 130. Specific materials, structures and construction of the biopsy valve 106, working channel port 208 and working tube 210 are known to those skilled in the art. The video port 108 comprises a suitable video connector 211, as further known to those skilled in the art. For example, the video connector 211 may comprise a pin and socket type connector, a pogo pin connector, card edge connector, etc. Preferably, the video connector 211 is a male connector configured to mate with a suitable female connector, though this is not a requirement. Though not shown in FIG. 2 for ease of illustration, the video connector 211 includes one or more cables (supporting operation of a light source and camera as noted above) connected thereto and extending through the rotary knob assembly 120 toward the distal end 132 of the insertion tube 130 in a manner similar to the working tube 210. Further still, the suction valve button 112 forms a portion of a suction valve body 202 extending out of the housing as shown. In turn, suction tubes 204, 206 are in fluid connection with the suction valve body 202 to the suction port 110 and working channel 210 (via the working channel port 208), thereby providing aspiration capability (under user-selectable control via the suction valve button 112) at the distal tip 132 of the insertion tube 130. Once again, suitable components, materials, dimensions, etc. for using in implementing the suction valve 202 and suction tubes 202, 204 are known to those skilled in the art.

Figure 3:
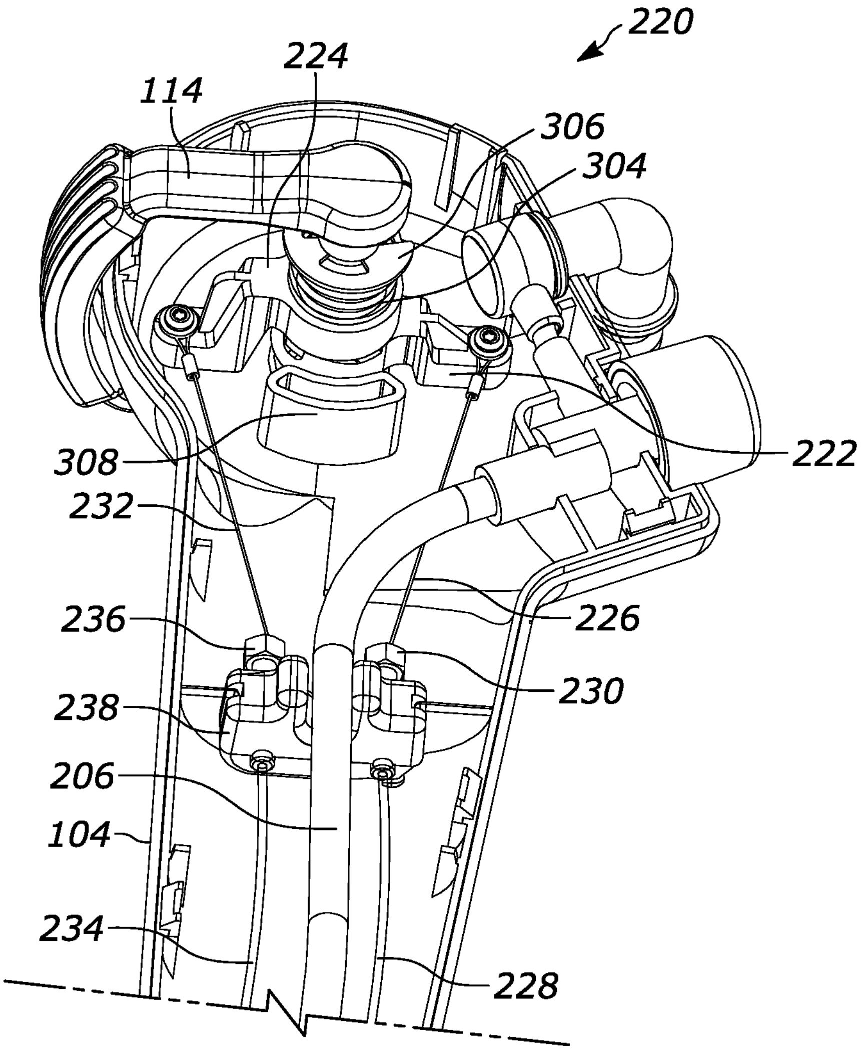
FIG. 3 is a bottom, side perspective view of the steerable medical device of FIGS. 1 and 2 in greater detail and further illustrating a control device in accordance with the instant disclosure in greater detail.
Figure 4:
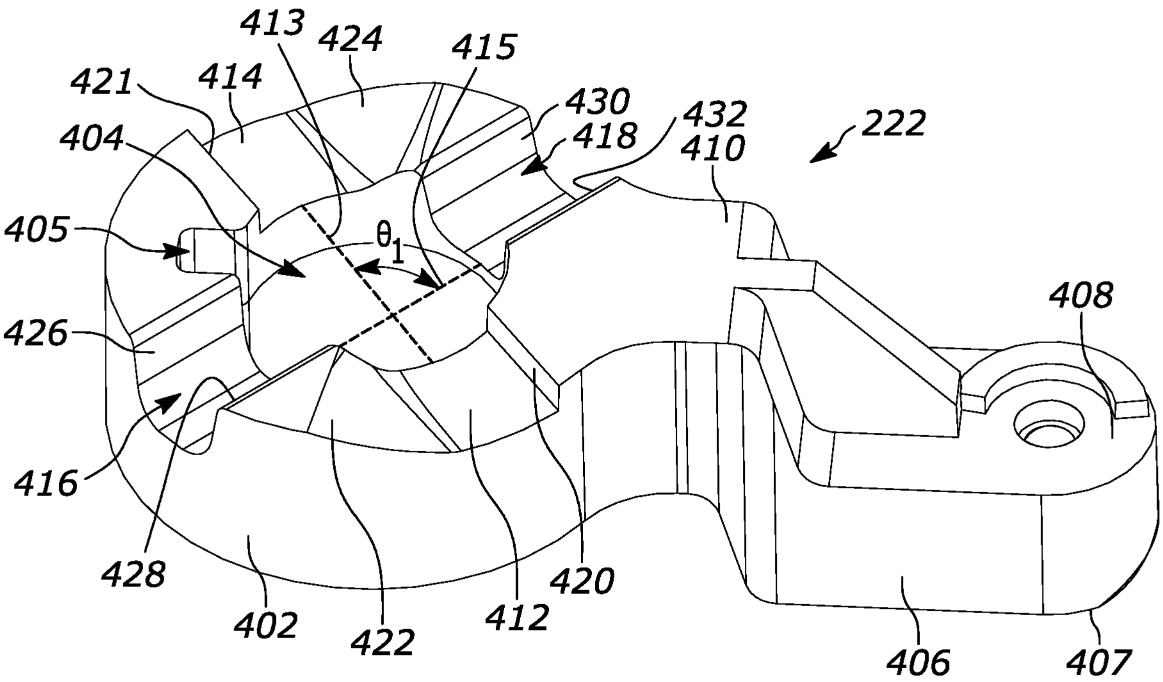
FIG. 4 is top, perspective view of a first steering cam of a control device in accordance with the instant disclosure.
Figure 5:
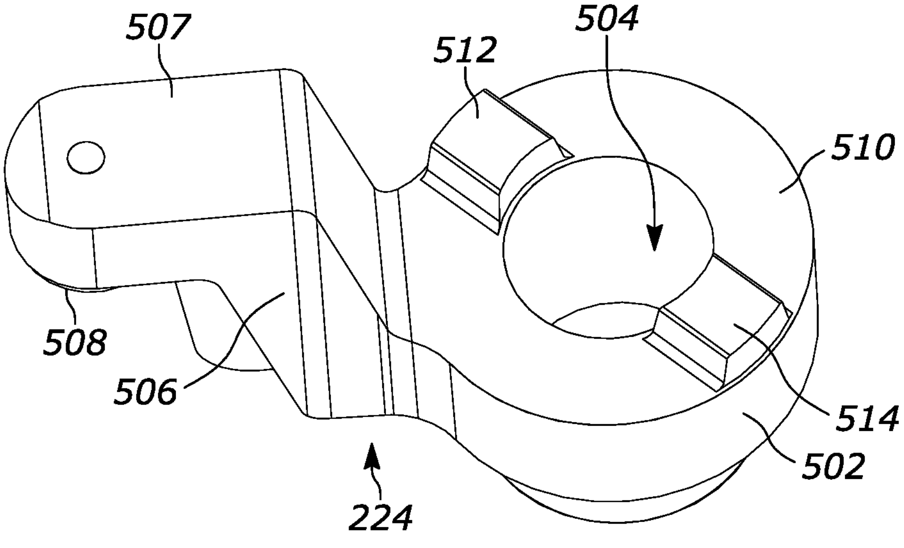
FIG. 5 is bottom, perspective view of a second steering cam of a control device in accordance with the instant disclosure.
Figure 6:
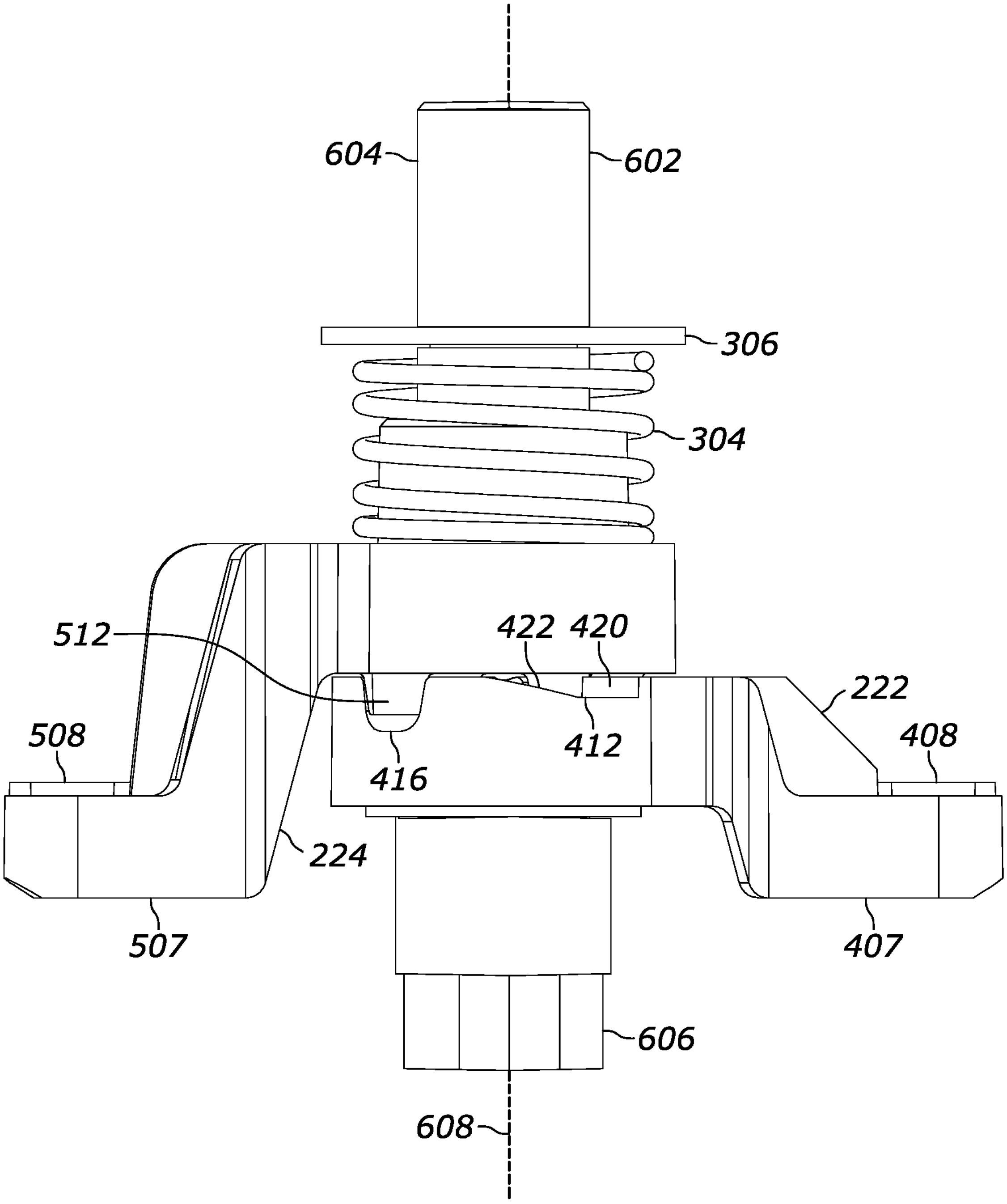
FIG. 6 is a more detailed side elevation view illustrating operation of a latch assembly of a control device in accordance with the instant disclosure.

As shown in FIG. 2, and in greater detail in FIG. 3-9, the housing has mounted thereon a control device 220 for use in controlling steering wires 226, 232. With reference to FIGS. 3 and 6, the control device 220 comprises a first steering cam 222 and a second steering cam 224 mounted on a steering shaft 602 that, in turn, is affixed to the user-controllable lever 114 such that rotation of the lever 114 also induces substantially similar rotation in the steering shaft 602. As shown in FIG. 6, the steering shaft 602 comprises a first end 604 and a second end 606, at least one of which is configured to extend outside of the housing, thereby permitting the affixed connection with the lever 114. For example, in the illustrated embodiment, the second end 606 comprises a keyed structure (in this case, a hexagonal outer surface) configured to extend out of the housing and to mate with a correspondingly keyed structure provided in an arm of the lever 114, where mating of the keyed structures permits rotation of the lever 114 to be applied to the steering shaft 602. In the illustrated example, the first end 604 of the steering shaft 602 is also configured to extend outside of the housing, though another arm of the lever 114, in this case, is only configured to contact the first end 604 as opposed to a mating connection in the case of the second end 606. However, it is appreciated that the second arm of lever 114 can also be configured to mate with the first end 604 of the steering shaft 602.

In an embodiment, the first steering cam 222 is affixed to the steering shaft 602 such that it rotates in unison with any rotation of the steering shaft 602 about a longitudinal axis 608 of the steering shaft 602. As shown in FIG. 4, the first steering cam 222 may include, in the illustrated example, a key slot 405 configured to mate with a complementary key protrusion formed on an outer surface of the steering shaft 602 (not shown). On the other hand, the second steering cam 224 is mounted on the steering shaft 602 but is freely rotatable about the longitudinal axis 608 of the steering shaft, i.e., independent of the steering shaft 602.

With reference to FIGS. 3-5, the first and second steering cams 222, 224 comprise respective first and second attachment portions 408, 508 configured to permit attachment of respective first and second steering wires 226, 232 thereto. In a presently preferred embodiment, the steering wires 226, 232 are constituent components of so-called Bowden cables 228, 234. As known in the art, Bowden cables 228, 234 are flexible cables having an inner wire 226, 232 surrounded by a hollow, helical winding cable housing. Bowden cables 228, 234 are particularly useful for the transmission of mechanical force via the inner wire 228, 232 relative to the cable housing. As used herein, the Bowden cables 228, 234 have their respective proximal ends of the cable housings terminated by tension adjustment screws 230, 236 mounted on a tensioning block 238 formed on the housing 104. Distal ends of the cable housings are terminated at a proximal end of the articulation section near the distal tip 132 of the insertion tube 130. The tensioning block 238 substantially prevents any longitudinal movement of the Bowden cables 228, 234 while permitting rotation of the tension adjustment screws 230, 236, thereby permitting tension of the inner wires (relative to the Bowden cable housings) to be set to a desired level. As described in further detail below, when a latch assembly provided by the first and second steering cams 222, 224 is in an active configuration, thereby placing the steering wires 226, 232 in a tensioned state, the tension adjusting screws may be adjusted during manufacturing/assembly of the steerable medical device 100 to permit final setting of a desired level of tension in the steering wires 226, 232 suitable for end use of the steerable medical device 100. However, following such tension setting, the latch assembly may be reconfigured to an inactive configuration in which the steering wires 226, 232 are maintained in an un-tensioned state during subsequent packaging, sterilization, shipping and storage steps. During final use, the latch assembly can once again be placed in the active configuration, thereby returning the steering cables 226, 232 back to the desired tension levels required for proper operation of the steerable medical device 100.

In a presently preferred embodiment, illustrated with further reference to FIGS. 4-6, the first steering cam 222 comprises a first circular body 402 having a first opening 404 formed therein and a first arm 406 radially extending therefrom. The second steering cam 224 is similarly constructed having a second circular body 502 having a second opening 504 formed therein and a second arm 506 radially extending therefrom. As described above, the first steering cam 222 included a key slot 405 formed on the internal surface defining the first opening 404, whereas the second steering cam 224 has no such key slot. The first steering cam 222 comprises a first facing surface 410 and the second steering cam 224 comprises a second facing surface 510 configured to be opposite the first facing surface 410 in use. In a presently preferred embodiment, both the first and second arms 406, 506 additionally extend longitudinally away from their respective first and second circular bodies 402, 502 but with respective underside surfaces 407, 507 that remain substantially parallel to their corresponding first and second facing surfaces 410, 510. Because, as best shown in FIG. 6, the second steering cam 224 is deployed above the first steering cam 222 when mounted on the steering shaft 602, the downward longitudinal extension of the second arm 506 is larger than the first arm 406 such that respective underside surfaces 407, 507 will occupy substantially the same plane when deployed, as shown in FIGS. 3 and 6. To provide effective cam operation (i.e., rotational to linear movement conversion), the first and second attachment portions 408, 508 are preferably provided toward respective distal ends of the first and second steering cams 222, 224. Furthermore, having the distal ends of the two arms 222, 224 designed so as to be located on substantially the same horizontal plane (as shown in FIG. 6 for example) permits the attached wires 226, 232 to be pulled evenly at the same angle (preferably parallel) relative to such horizontal plane.

Features of the first and second steering cams 222, 224 may be provided to implement the above-noted active and inactive configurations of a latch assembly. Thus, in FIG. 4, the first steering cam 222 includes, formed on and into the first facing surface 410, at least one inactive notch 412, 414 and at least one active notch 416, 418 angularly spaced apart from each other. For example, in the illustrated embodiment, the first facing surface 410 comprises two diametrically opposed inactive notches 412, 414 and two diametrically opposed active notches 416, 418, where diameter lines 413, 415 across the circular body 402 and connecting centerlines of the inactive notches 412, 414 pair and active notches 416, 418 pair are separated by a non-zero angle, $\theta_1$, where $\theta_1$ is preferably in the range of 10-80° and even more preferably in the range of 40-60°. As will be evident from the description below, the angular separation, $\theta_1$, between the at least one inactive and at least one active notch determines the amount of rotation (under control of the user-controlled lever 114) necessary to switch the latch assembly from the inactive to active configurations and vice versa. Preferably, the widths of the inactive 412, 414 and active 416, 418 notches (i.e., the distances between the bases of sidewalls 420-424 for the inactive notches 412, 414 and the distances between sidewalls 426-432 for the active notches 416, 418) are substantially the same.

As further shown in FIG. 4, respective depths of the at least one inactive notch 412, 414 and the at least one active notch 416, 418 are different, where the depth of the at least one inactive notch 412, 414 is less than (i.e., shallower) than the depth of the at least one active notch 416, 418. In an embodiment, sidewalls 426-432 defining the at least one active notch 416, 418 are substantially vertical along their depth. On the other hand, in this embodiment, only one of the sidewalls 420, 421 defining the at least one inactive notch 412, 414 is substantially vertical along its depth, whereas the other sidewall 422, 424 defining the at least one inactive notch 412, 414 is formed at a relatively shallow angle (i.e., is sloped) as compared the other substantially vertical sidewalls 420, 421, 426-432. As described below, this sloping of only one sidewall 420, 421 of the at least one inactive notch 412, 414 facilitates rotation of first and second steering cams 222, 224 relative to each other in one direction as opposed to another.

In keeping with the embodiment illustrated in FIG. 4, and as shown in FIG. 5, the second steering cam 224 includes at least one projection 512, 514 formed on and away from the second facing surface 510. In the example illustrated in FIG. 5, the second facing surface 510 comprises two diametrically opposed projections 512, 514 configured to mate with the inactive notches 412, 414 when aligned therewith, and to mate with the active notches 416, 418 when aligned therewith. Additionally, the projections 512, 514 are configured to have heights, in a presently preferred embodiment, substantially matching the depths of the two active notches 416, 418. In this manner, mating alignment of the protrusions 512, 514 with corresponding ones of the active notches 416, 418 (i.e., when the first and second facing surfaces 410, 510 are opposite and in contact with each other) will cause the first and second steering cams 222, 224 to be essentially rotationally "locked" together, as illustrated in FIG. 6. Also note that, in the illustrated preferred embodiment, the angular alignment of the protrusions 512, 514 relative to the second arm 506 is substantially identical to the angular alignment of the active notches 416, 418 to the first arm 406 such that engagement of the protrusions 512, 514 with corresponding ones of the active notches 416, 418 will result in the first and second arms 406, 506 being diametrically opposed to each other as further shown in FIG. 6.

Figure 8:
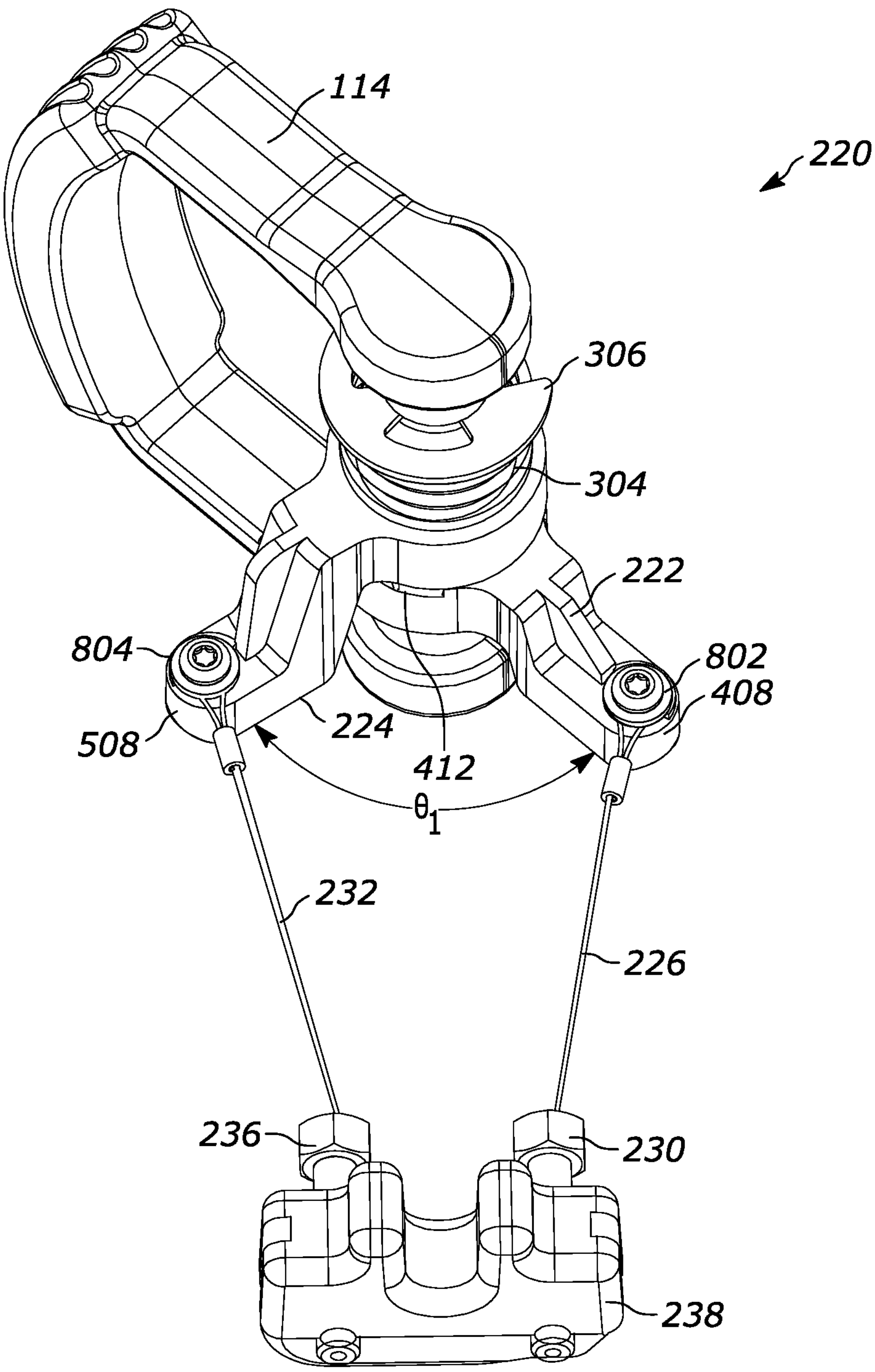
FIG. 8 is bottom, perspective view of a control device in an inactive configuration in accordance with the instant disclosure.

On the other hand, when the protrusions 512, 514 are aligned with corresponding ones of the inactive notches 412, 414, as shown in FIG. 8, the first and second arms 406, 506 will be separated by the same angle, $\theta_1$, described above. It is noted that the unequal longitudinal extent of the respective arms, as best shown in FIG. 6, and assuming continuous contact of the first and second facing surfaces 410, 510, would prevent the situation in which the first and second arms 222, 224 are angularly aligned with each other. Furthermore, rotation of the first steering cam 222 (for example, by virtue of rotation of the lever 114) such that the substantially vertical sidewalls 420, 421 are biased toward respective ones of the engaged protrusions 512, 512 will resist disengagement of the protrusions 512, 514 from the inactive notches 412, 414 to the extent that the vertical sidewalls 420, 421 do not facilitate sliding contact with the protrusions 512, 514. On the other hand, rotation of the first steering cam 222 such that the sloped sidewall 422, 424 are biased toward respective ones of the engaged protrusions 512, 512 will more readily permit disengagement of the protrusions 512, 512 from the inactive notches 412, 414 to the extent that the sloped sidewalls 422, 424 facilitate sliding contact with the protrusions 512, 514.

Although the description above concerning the first and second steering cams 222, 224 is based on the provision of notches 412-418 only on the first facing surface 410 and the protrusions 512, 514 only on the second facing surface 510, it will be appreciated that this is not a requirement. For example, a combination of a diametrically opposed notch and protrusion could be provided on the first facing surface 410 while a similar but oppositely configured combination of another diametrically opposed notch and protrusion could be provided on the second facing surface 510. It is noted that the instant disclosure is not limited to the illustrated notch/protrusion design; for example, a different combination of diametrically opposed geometric shapes could be equally employed. Furthermore, the inactive notches could be replaced with simple horizontal positions (i.e., no notches at the inactive position) for the protrusions to rest on in the inactive state. In this case, to prevent the cams 222, 224 from inadvertently engaging during sterilization, transportation or storage, movement of the user-controllable lever 114 can be prevented with a suitable plastic cap or by placing the device 100 in a packaging tray with complementary shape to receive the device 100 and maintain the user-controllable lever 114 in the desired position.

Figure 7:
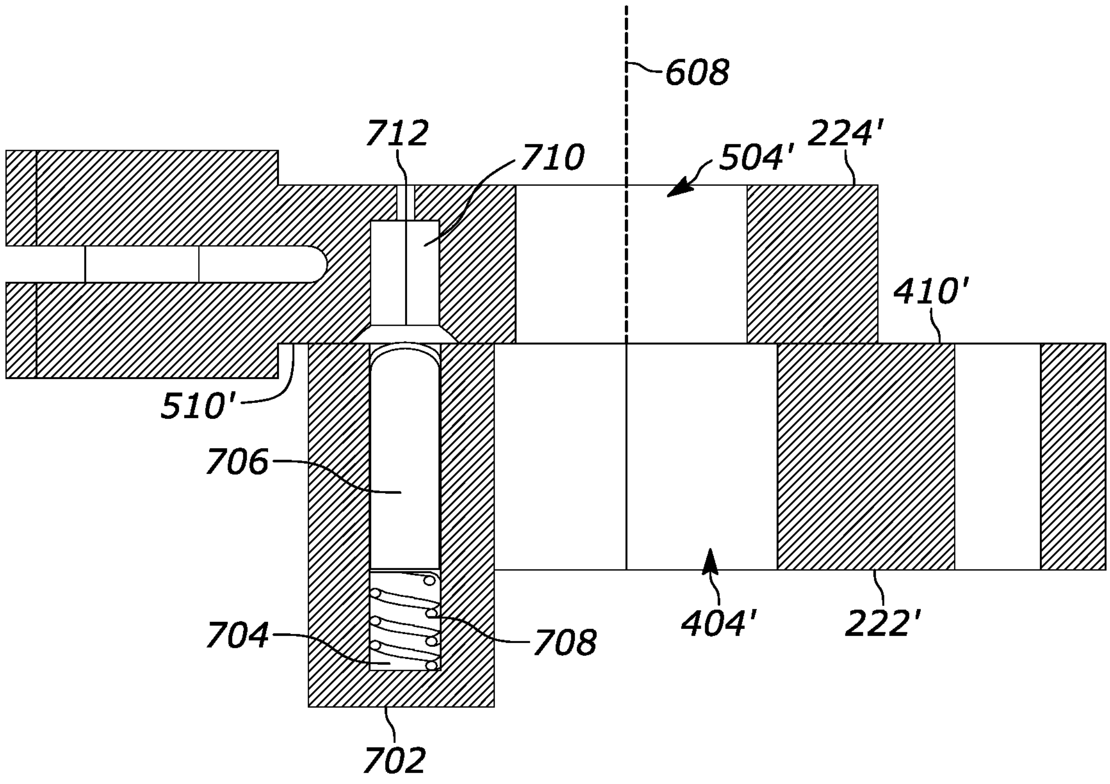
FIG. 7 is a cross-sectional view of an alternative embodiment of a latch assembly of a control device in accordance with the instant disclosure.

As an option to the latch assembly provided by the notches and protrusion arrangement of the first and second steering cams 222, 224 illustrated in FIGS. 4-6, FIG. 7 illustrates an alternative latch assembly in which a first steering cam 222' includes a boss 702 having a first vertical bore 704 formed therein and open to the first facing surface 410' of the first steering cam 222'. A pin 706 is disposed in the first vertical bore 704 and biased out of the first vertical bore 704 by a spring 708 disposed between the pin 706 and an end face of the first vertical bore 704. In this embodiment, the second steering cam 224' has a second vertical bore 710 formed therein and open to the second facing surface 510' of the second steering cam 224'. As shown, the second vertical bore 710 is substantially the same radial distance away from the longitudinal axis 608 of the steering shaft (not shown in FIG. 7). Furthermore, the second vertical bore 710 preferably has an inner diameter substantially equal to an outer diameter of the pin 706 and, in any event, sufficiently wide to permit rapid entrance of the pin 706 into the second vertical bore 710 (under the bias of the spring 708) when the first and second vertical bores 704, 710 are aligned. Insertion of the pin 706 into the second vertical bore 710 once again rotationally locks the second steering cam 224' to the first steering cam 222'. To facilitate disengagement of the first and second steering cams 222', 224', a pin hole 712, aligned with the second vertical bore 710 is provided in the end wall of the second vertical bore 710 as shown in FIG. 7. Insertion of a rigid pin or other small diameter tool into the pin hole 712 allows an opposing force greater than the bias force of the spring 708 to be applied to the pin 706, thereby causing the pin 706 to withdraw from the second vertical bore 710 and back into the first vertical bore 704. When the pin is fully disengaged from the second vertical bore 710, the second steering cam 224' is once again free to rotate about the steering shaft independent of the first steering cam 222'.

Regardless of its implementation, operation of the latch assembly illustrated in FIGS. 4-7 is based on the assumption that first and second facing surfaces 410, 410', 510, 510' are continuously maintained in contact with each other. To that end, in a presently preferred embodiment, a biasing element may be provided to bias the first and second steering cams 222, 224 into contact with each other. More specifically, in the example best shown in FIGS. 3 and 6, a spring 304 is deployed about the steering shaft 602 between the second steering cam 224 and a C-clip 306 or the like attached to the steering shaft 602 along an annular groove (not visible) formed in the steering shaft 602. The reaction surface provided by the C-clip 306 causes the spring 304 to bias the second steering cam 224 into contact with the first steering cam 222. As will be appreciated by the skilled person, other resilient elements and arrangements thereof may be provided to similarly bias the steering cams 222, 224 toward each other.

Figure 9:
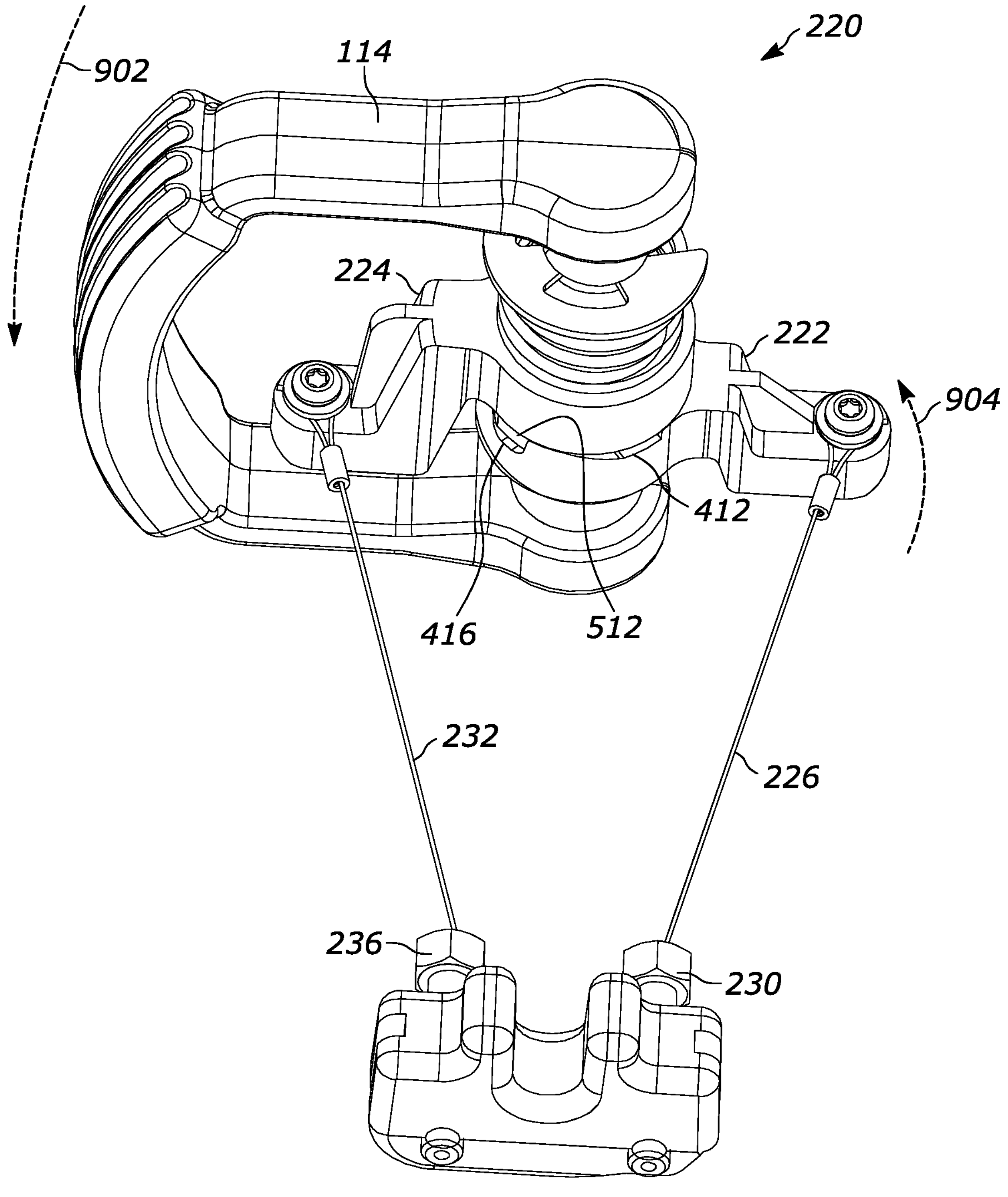
FIG. 9 is bottom, perspective view of a control device in an active configuration in accordance with the instant disclosure.

Referring now to FIGS. 8 and 9, operation of a control device 220 in accordance with the instant disclosure is further illustrated. In particular, FIG. 8 illustrates an inactive configuration of the latch assembly provided by the first and second steering cams 222, 224, i.e., when the protrusions 512, 514 are aligned with the inactive notches 412, 414 as described above. In this inactive state, the first and second steering cams 222, 224 are positioned such that the first and second steering wires 226, 232 are maintained in a relatively un-tensioned (or reduced tension) state, i.e., in a state of tension that would not provide for proper control of the distal tip 132 of the insertion tube 130. Additionally, stop surfaces provided by a pillar 308 (FIG. 3) may also be provided to prevent further rotation of the latch assembly 220 when in the inactive state.

On the other hand, FIG. 9 illustrates an active configuration of the latch assembly provided by the first and second steering cams 222, 224, i.e., when the protrusions 512, 514 are aligned with the active notches 416, 418 as described above. As shown in FIG. 9, the active configuration is achieved when a user actuates (rotates) 902 the lever 114 as shown, thereby inducing a corresponding rotation 904 of the first steering cam 222. Simultaneously, the existing tension on the second steering wire 232 when in the inactive configuration/un-tensioned state maintains the second (freely rotatable) steering cam 224 is its original position. When the first steering cam 222 has rotated a sufficient amount to provide alignment of the protrusions 512, 514 and the active notches 416, 418, the first and second steering cams 222, 224 are locked together as described above. In this activated configuration, both the first and second steering wires 226, 232 are placed in a tensioned state, i.e., in a state of tension greater than the un-tensioned state shown in FIG. 8. During manufacturing and assembly of the steerable medical device 100, placement of the steering wires in the tensioned state shown in FIG. 9 permits adjustment (through use of the tensioning adjustment screws 230, 236 as described above) to achieve a final, desired level of tensioning, i.e., sufficient to provide accurate and reliable control of the distal tip 132 of the insertion tube 130.

Thus, during manufacturing/assembly, the first and second steering cams 222, 224 will be positioned as illustrated in FIG. 9, thereby permitting proper tensioning of the steering wires 226, 232. Once final tensioning levels have been achieved (but prior to packaging, sterilization, shipment and storage) a suitable tool may be used to apply a larger counter force against the bias provided by the spring 306, thereby permitting the first and second steering cams 222, 224 to be unlocked from each other, i.e., for the protrusions 512, 514 to become disengaged from the active notches 416, 418. In this case, the tension of the steering wires 226, 232 and/or through appropriate rotation of the lever 114 (clockwise as shown in FIGS. 8 and 9) will cause the first and second steering cams 222, 224 to rotate toward the inactive configuration shown in FIG. 8, thereby permitting the protrusions 512, 514 to engage the inactive notches 412, 414. Once the first and second cams 222, 224 are placed in the inactive state, thereby reducing tension applied to the steering cables 226, 232, the steerable medical device 100 may be subjected to the necessary packaging, sterilization, shipping and storage processes without fear that such processes will cause any undesired deformation of the distal tip 132, as described above. Due to the engagement of the protrusions 512, 514 and the inactive notches 412, 414, the steering wires 226, 232 will remain in the reduced tension state until such time (e.g., end use by medical personnel) that the lever 114 is rotated as shown in FIG. 9, thereby once again causing the protrusions 512, 514 to engage the active notches 416, 418. Because of the final tensioning set by the tension adjustment screws 230, 236 during manufacturing and assembly, the return of the first and second cams 222, 224 will re-tension the steering cables 226, 232 to their final adjusted state. Additionally, because the first and second cams 222, 224 are now once again locked together, further rotations of the lever 114 in either direction will cause the desired deflections of the distal tip 132 when in use.

Figure 10:
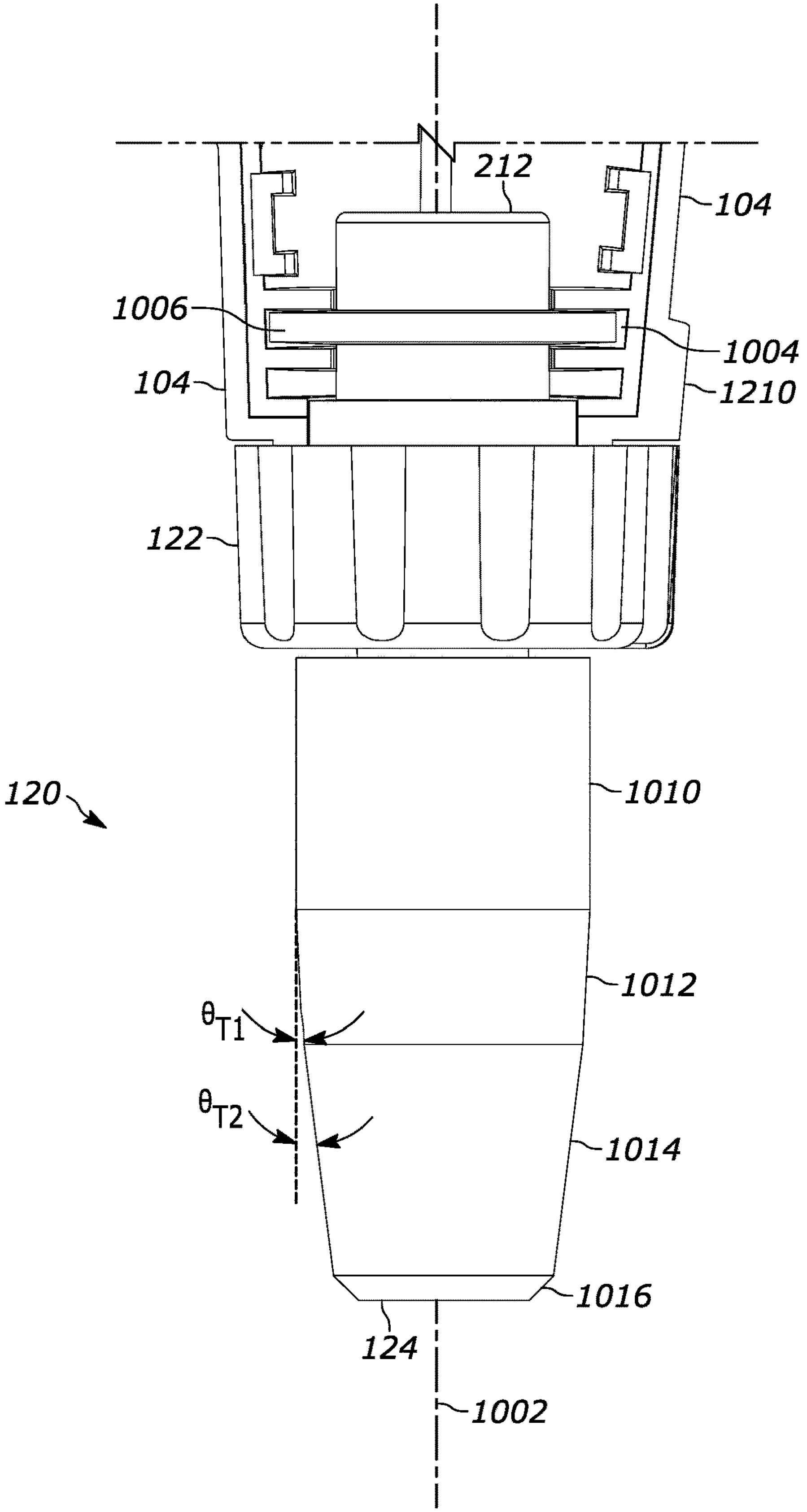
FIG. 10 is a side elevation view of a rotary knob assembly in accordance with the instant disclosure.
Figure 11:
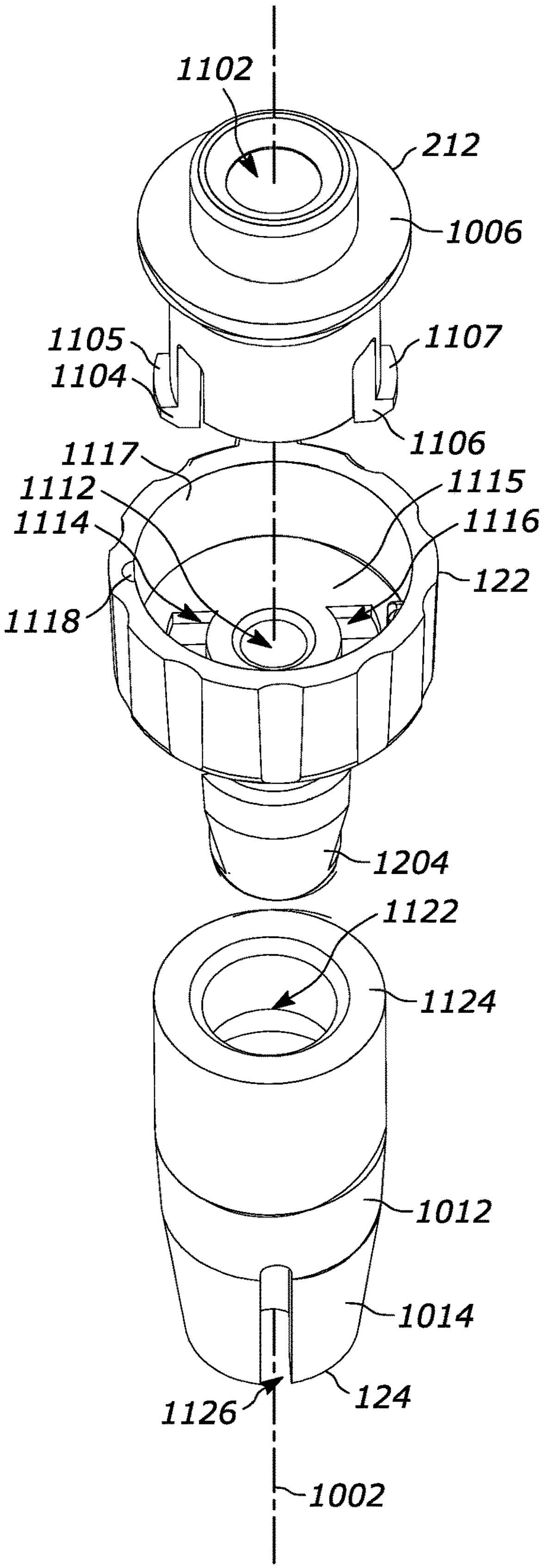
FIG. 11 is a top, perspective exploded view of a knob assembly in accordance with the instant disclosure.
Figure 12:
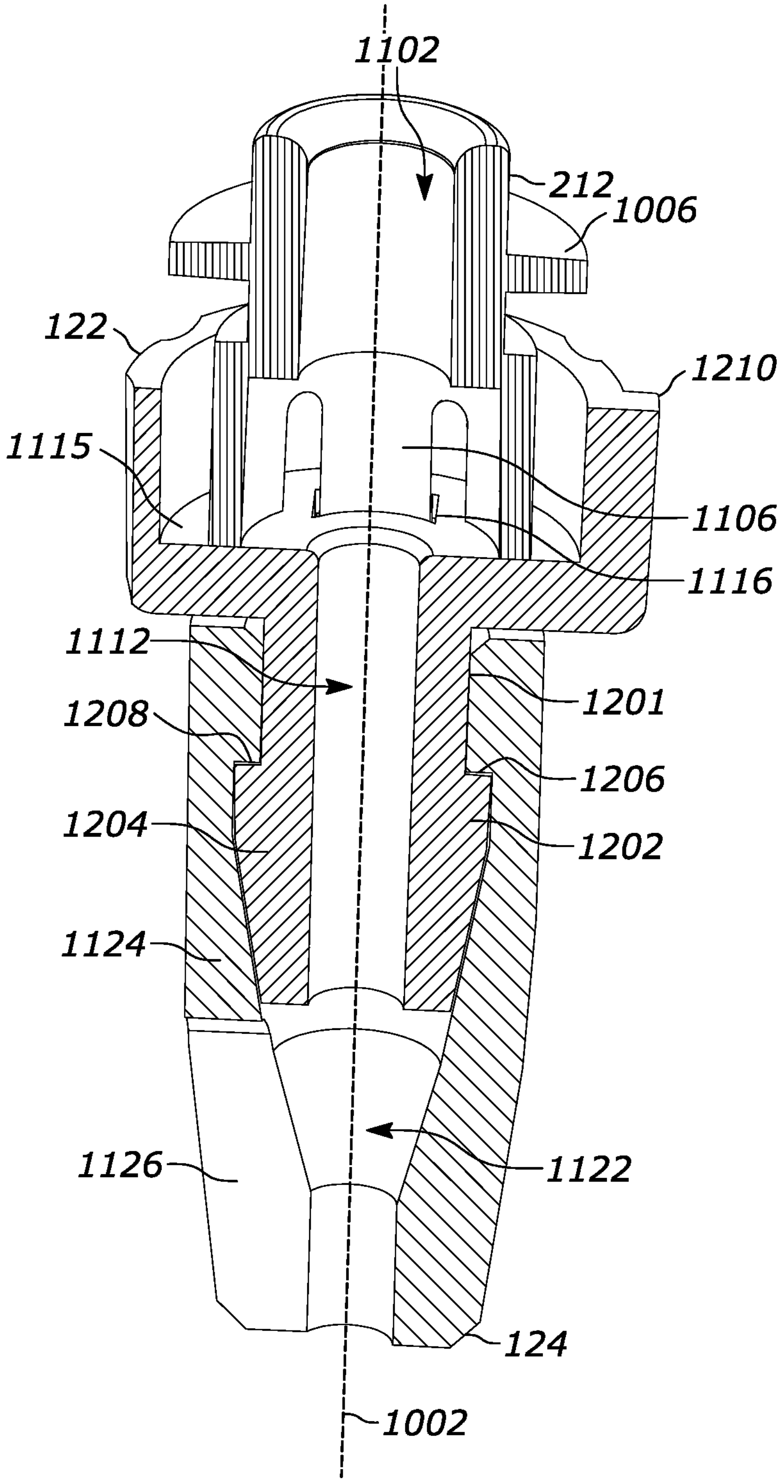
FIG. 12 is a top, perspective cross-sectional view of a knob assembly in accordance with the instant disclosure.
Figure 12A:
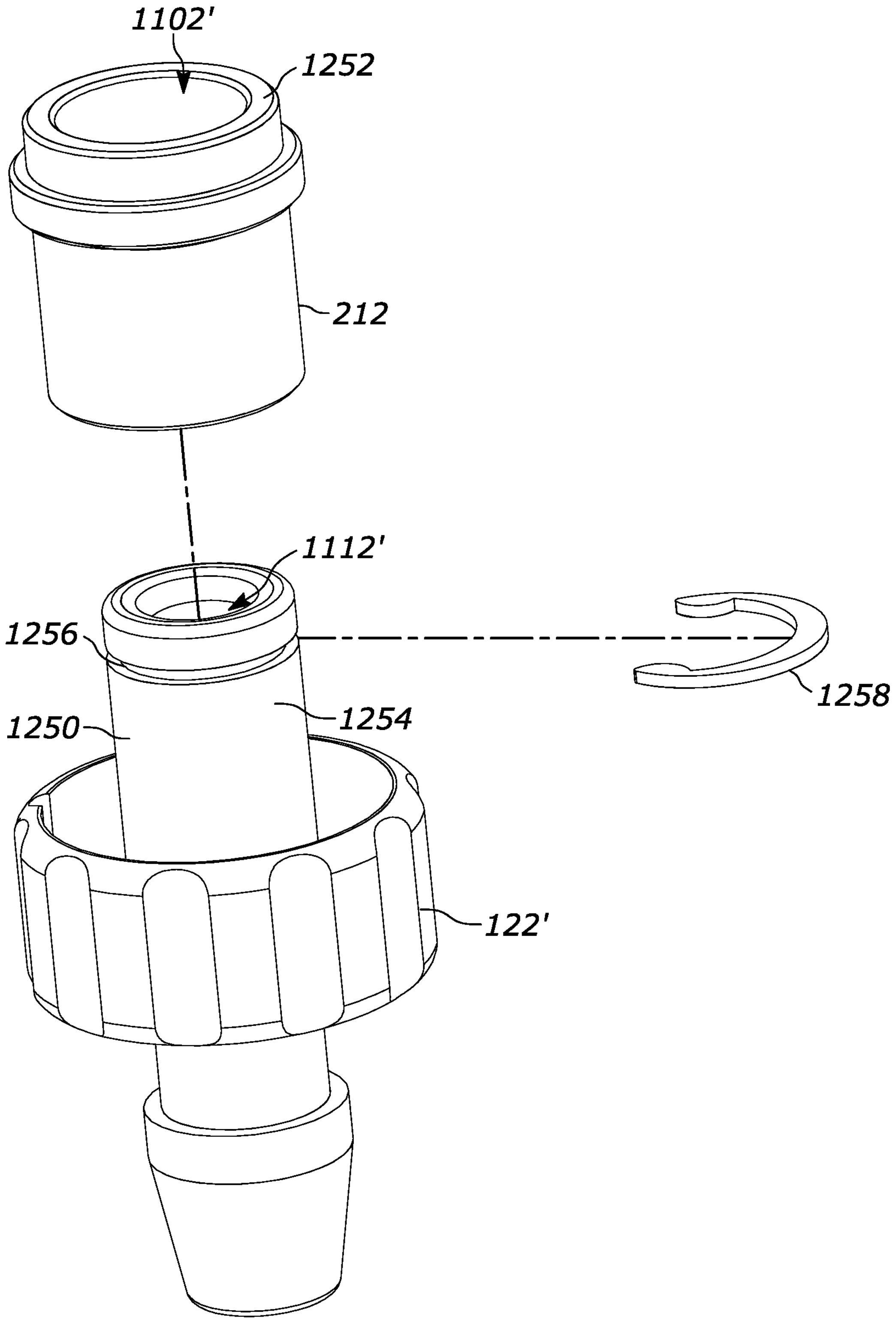
FIG. 12A is side, perspective exploded view of a knob assembly in accordance with an alternate embodiment of the instant disclosure.

Further description of the rotary knob assembly 120 is provided with reference to FIGS. 10-15. In particular, the rotary knob assembly 120 comprises a bushing 212 rotatably mounted on the housing 101 such that the bushing 212 is permitted to freely rotate about a longitudinal axis 1002 of the housing 101. The bushing 212 comprises a longitudinal opening 1102 formed therein and configured to be centered on the longitudinal axis 1002. In the illustrated embodiment, the bushing 212 comprises a radially extending flange 1006 configured for engagement with an annular channel 1004 formed in the housing 101. The user controllable knob 122 is affixed to the bushing 212 and, in turn, the endotracheal tube retainer 124 is affixed to the knob 122. As best shown in FIGS. 11 and 12, the knob 122 is affixed to the bushing 212 through engagement of cantilevered arms 1104, 1106 with corresponding holes 1114, 1116 formed in a bottom surface 1115 of the knob 122. When the arms 1104, 1106 are fully inserted into their corresponding holes 1114, 1116, radially extending fingers 1105, 1107 formed on distal ends of the arms 1104, 1106 engage with a corresponding lip 1502, 1504 (FIG. 15) of the holes 1114, 1116 thereby preventing removal of the knob 122 from the bushing 122 and further allowing the knob 122 to rotate in unison with the bushing 212. Other configurations for attaching the knob 122 to the bushing 212 may be equally employed. For example, and as illustrated in FIG. 12A, instead of cantilevered arms 1104, 1106 extending downward from the bushing 212, the knob 122' could have an upwardly extending tubular section 1250 (having a longitudinal opening 1112') configured to concentrically fit within the longitudinal opening 1102' of the bushing 212', which tubular section 1250 could extend longitudinally such that it extends past an upper surface 1252 of the bushing 212'. In this case, an outer surface 1254 of the upwardly extending tubular section 1250 could include an annular channel 1256 configured to receive a C-clip 1258 that would retain the tubular section 1250 in its longitudinal relationship with the bushing 212' such that the knob 122' cannot be displaced from the bushing 212' but still retain rotational freedom about the longitudinal axis 1002 of the housing 101. Further attachment configurations, readily conceived by the skilled person, may be equally employed.

As best shown in FIG. 12, the knob 122 further comprises a tubular section 1201 longitudinally extending downward from its bottom surface 1115 and forming another longitudinal opening 1112 configured to be centered on the longitudinal axis 1002 when the knob 122 is affixed to the bushing 212. As shown, the tubular section 1201 comprises radially-extending barbs 1202, 1204. In turn, the endotracheal tube retainer 124 is formed such that sidewalls 1124 form yet another longitudinally extending opening 1122 also configured to be centered on the longitudinal axis 1002 when the tube retainer 124 is affixed to the knob 122. As shown in FIG. 12, the tube retainer 124 may comprise shoulders 1206, 1208 formed on an inner surface of the sidewall 1124 and configured to engage the barbs 1202, 1204 of the tubular section 1201, thereby affixing the tube retainer 124 to the knob 122.

In a presently preferred embodiment, the tube retainer 124 is fabricated from a suitable elastomer such as polyurethane, silicone, polyisoprene, polychloroprene, polybutadiene, acrylonitrile butadiene rubber, styrene block copolymer, polyvinylchloride and other thermoplastic elastomers, preferably with a hardness range of 20-100 durometer shore A and even more preferably with a hardness range of 40-90 durometer shore A, thereby permitting rapid and reliable attachment of, for example, endotracheal tubes or the like through the frictional engagement of the inner surfaces of the tracheal tube connectors. As known in the art, while such endotracheal tubes or other tracheal tubes have ISO connectors with standard outer diameters, the inner diameters of such standard connectors vary with wall thicknesses, which, in turn, sometimes makes attachment to the steerable medical device 100 difficult. The tube retainer 124 may include features to better facilitate the attachment of such tubes. For example, as best shown in FIGS. 11 and 12, the tube retainer 124 may include longitudinally-extending slot 1126 in its sidewall 1124. In the example shown in the Figures, the slot 1126 extends about one-quarter to one-half the length of the tube retainer 124. Furthermore, as shown, the slot 1126 extends fully through the thickness of the sidewall 1124, thereby permitting communication between the opening 1122 of the tube retainer 124 and its outer diameter, though this is not a requirement and the slot 1126 could extend through less than the total thickness of the sidewall 1124. The presence of the slot 1126 permits the sidewall 1124 of the tube retainer 124 to be slightly deformed and compressed when attaching an endotracheal tube connector or the like, thereby accommodating potentially varying inner tube diameters. Additionally, though the Figures illustrate only a single slot 1126, it is appreciated that more than one such slot, for example angularly spaced about the circumference of the tube retainer 124, may be incorporated into the sidewall 1124 thereof.

Furthermore, as best shown in FIG. 10, the tube retainer 124 may include one or more outer surface taper angles to facilitate tube attachment. For example, in the illustrated embodiment, the outer surface tube retainer 124 is characterized by four distinct portions: a straight portion 1010 at an end of the tube retainer 124 proximal to the knob 122, followed in succession along the length of the tube retainer 124 by a first tapered section 1012, a second tapered section 1014 and a chamfered or beveled portion 1016. As shown, the external surface of the straight portion 1010 is substantially vertical or parallel to the longitudinal axis 1002 of the housing 101. In turn, the external surface of the first tapered section 1012 substantially forms an angle, $\theta_{T1}$, relative to the vertical or longitudinal axis 1002 and the external surface of the second tapered section 1012 substantially forms an angle, $\theta_{T2}$, relative to the vertical or longitudinal axis 1002, where $\theta_{T1}<\theta_{T2}$. Finally, the chamfered or beveled portion 1016 provides a transition from the outer diameter of the sidewall 1124 to the inner diameter of the opening 1122. The first and second tapered sections 1012, 1014 provide for stepped transitions to the outer diameter 1010 of the tube retainer 124, thereby once again accommodating the possibility of endotracheal tube connectors or similar attachments having different internal diameters. In a presently preferred embodiment, the first taper angle, $\theta_{T1}$, is in the range of 3-4 degrees, whereas the second taper angle, $\theta_{T2}$, is in the range of 7-8 degrees, though it is understood that other angle ranges may be employed as a matter of design choice. Additionally, though not shown, the external surface of the tube retainer 124 may be textured to further facilitate tube attachment.

Regardless, when the rotary knob assembly 120 is fully assembled, the composite structure of the bushing 212, knob 122 and tube retainer 124 is freely rotatable about the longitudinal axis 1002 of the housing 101, subject to the limitations described below. Further, the alignment of the openings 1102, 1112, 1122 about the longitudinal axis 1002 provides a continuous channel throughout the entire length of the rotary knob assembly 120, thereby permitting passage of the steering wires 226, 232 and other components out of the housing 101 as described above.

Figure 13:
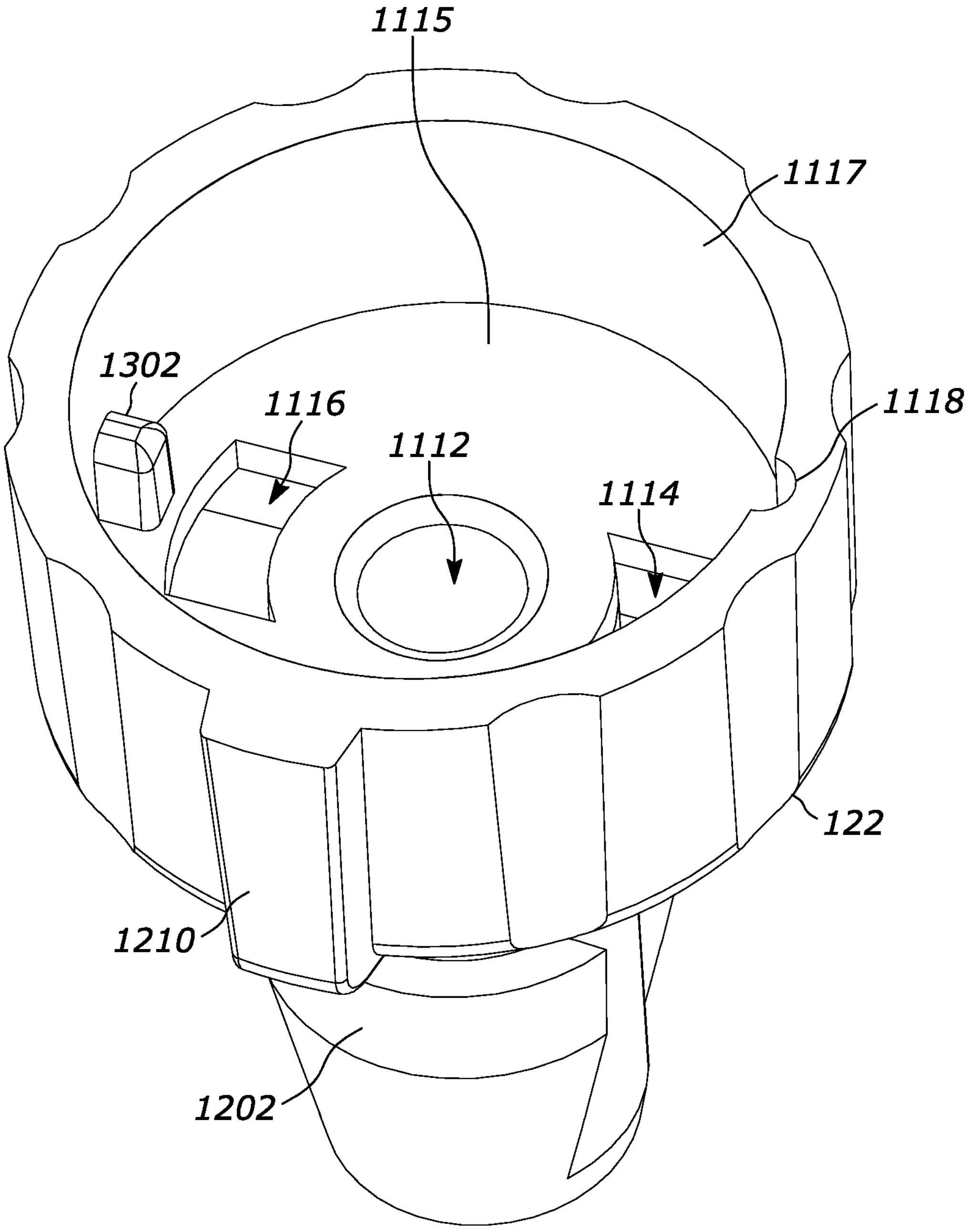
FIG. 13 is a top, perspective view of a user-controllable knob in accordance with the instant disclosure.

Further features of the knob 122 and housing 101 are further illustrated with reference to FIGS. 11-15. In particular, the knob 122 includes, as best shown in FIGS. 11, 13 and 15, a recess 1118 formed in an interior surface 1117 of a sidewall forming the knob 122. Further, as best shown in FIGS. 12, 13 and 15, the knob 122 also includes a knob zero-position indicator 1210 on an outer surface of the knob 122 and angularly spaced, in the illustrated embodiment, 90° away from the recess 1118. Further still, as best shown in FIGS. 13 and 15, the knob 122 also includes a knob stop surface 1302 formed, in the illustrated embodiment, as a radially inward projecting protrusion formed at the intersection of the bottom surface 1115 and interior surface 1117, and diametrically opposed to the recess 1118.

Figure 14:
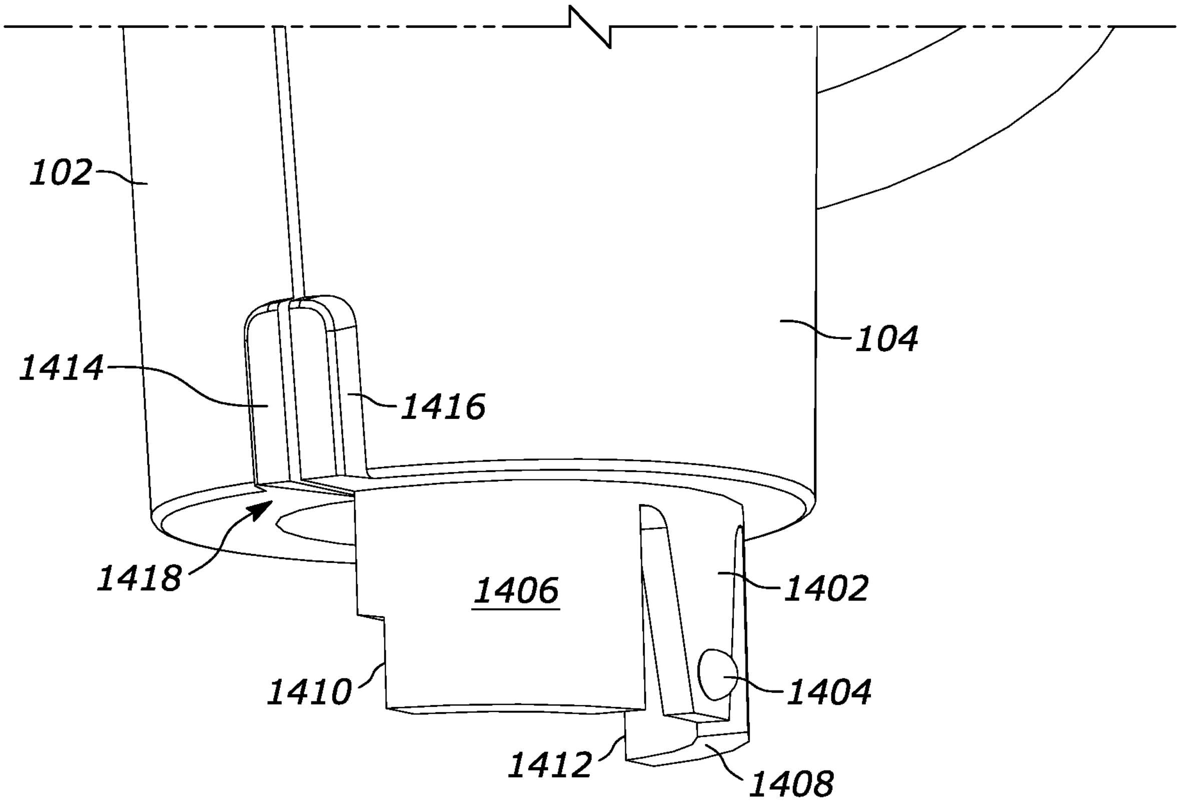
FIG. 14 is a bottom, perspective view illustrating features a housing for use with a rotary knob assembly in accordance with the instant disclosure.
Figure 15:
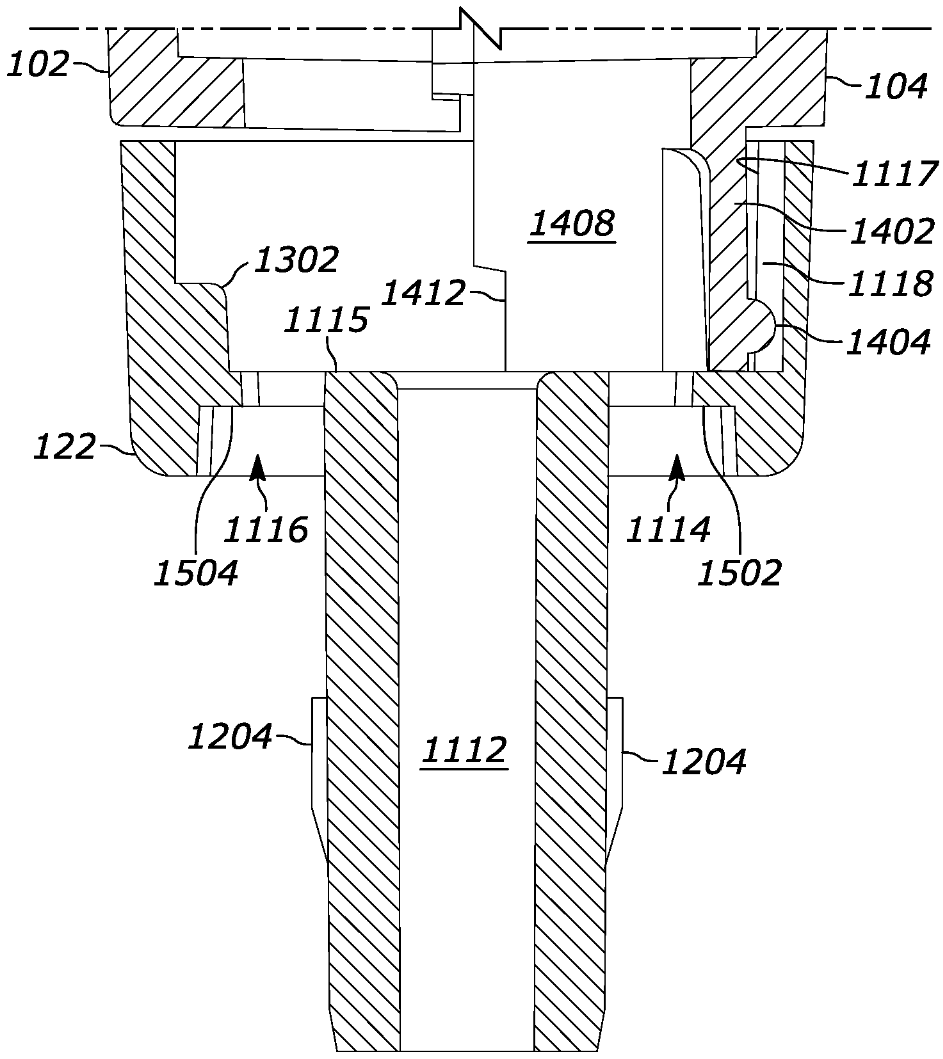
FIG. 15 is cross-sectional view of user-controllable knob and housing in accordance with the instant disclosure.

Features for interacting with the recess 1118, knob zero-position indicator 1210 and knob stop surface 1302 are incorporated into the housing 101 as best illustrated in FIGS. 14 and 15. First, each housing portion 102, 104 comprises a protrusion 1414, 1416 formed at lower or distal edges of each portion 102, 104 and radially extending outward from outer surfaces of each housing portion 102, 104. When the housing portions 102, 104 are joined together, as shown in FIG. 14, they collectively form a housing zero-position indicator 1418. Further, the second housing portion 104 comprises radially recessed sidewalls 1406, 1408 extending downwardly from a lower or distal edge of the first housing portion 104. Outer surfaces of the recessed sidewalls 1406, 1408 are configured to conform to the inner surface 1117 of the knob without substantially contacting the inner surface 1117. On the other hand, a cantilevered arm 1402, formed between and at the same radial distance as the recessed sidewalls 1406, 1408, is provided with an outwardly projecting detent 1404 at a distal end of the arm 1402. It is noted that the arm 1402 and detent 1404 are formed at a 90° separation from the housing zero-position indicator 1418 in the same manner that the recess 1118 and knob zero-position indicator 1210 are also formed at a 90° separation from each other. The detent 1404 is configured to radially extend outward to a sufficient degree that it will interfere with the inner surface 1117 of the knob 122 unless aligned with the recess 1118. The combined angular extent of the recessed sidewalls 1406, 1408 and the arm 1402 is preferably coextensive with that of the second housing portion 104, i.e., approximately 180°. However, as shown in FIGS. 14 and 15, housing stop surfaces 1410, 1412 are formed in the respective first and second recessed sidewalls 1406, 1408 such that angle from the first housing stop surface 1410 to the second housing stop surface 1412 is slightly less than 180°, for example 160°-180°.

As best shown in FIG. 15, illustrating the housing portions 102, 104 but not the bushing 212, when the arm 1402 and detent 1404 are aligned with the recess 1118, the detent 1404 will extend past the inner surface 1117 of the knob 122 and into the space defining the recess 1118. In this position, given the respective 90° separations between the recess 1118 and knob zero-position indicator 1210 on the one hand, and between the arm 1402/detent 1404 and housing zero-position indicator 1418 on the other, the respective zero-position indicators 1210, 1418 will substantially align with each other. In this manner, a user of the steerable medical device 100 is provided with a visual indication that the knob 122 is in a zero-rotation (or default) position. Furthermore, as the knob 122 is rotated away from its zero-rotation position, interaction of the detent 1404 and recess 1118 will provide initial, low force resistance to such rotation until the arm 1402 is caused to flex inwardly, thereby releasing the engagement of the detent 1404 and the recess 1118 and causing the detent to thereafter interfere with the inner surface 1117. In this manner, a user of the medical device is provided with haptic feedback indicating that the user is rotating away from the zero-rotation position. In a similar vein, rotation of the knob 122 toward the zero-rotation position will eventually cause the detent 1404, under bias applied by the flexed arm 1402, to snap back into engagement with the recess 1118, which may provide either an audible sound signaling such re-engagement and/or an increased resistance to further rotation as another form of haptic feedback.

Additionally, when the arm 1402 and detent 1404 are aligned with the recess 1118, both of the housing stop surfaces 1410, 1412, which each extend upwardly from the bottom surface 1115 of the knob 122, each of the housing stop surfaces 1410, 1412 is substantially positioned at a maximum angular difference (90° in the illustrated example) from the knob stop surface 1302. This is best illustrated in FIG. 15 where the separation between the second housing stop surface 1412 and the knob stop surface 1302 is shown. As the knob 122 is rotated in either direction, one or the other of the housing stop surfaces 1410, 1412 will gradually be rotated toward the knob stop surface 1302 until the housing stop surface 1410, 1412 engages with the knob stop surface 1302, thereby preventing further rotation of the knob 122. In this manner, a user of the steerable medical device is provided with affirmative feedback that the full extent of rotation (in this case, 90°) in that direction has been reached. Thought the illustrated example shows housing stop surfaces 1410, 1412 providing 90° rotation capability in either direction, it is appreciated that different angular extents of the recessed sidewalls 1406, 1408 and, consequently, positioning of such stop surfaces 1410, 1412 could be employed to provide rotation capabilities in either direction that are greater (up to 180°) or less than 90°.

Figure 16:
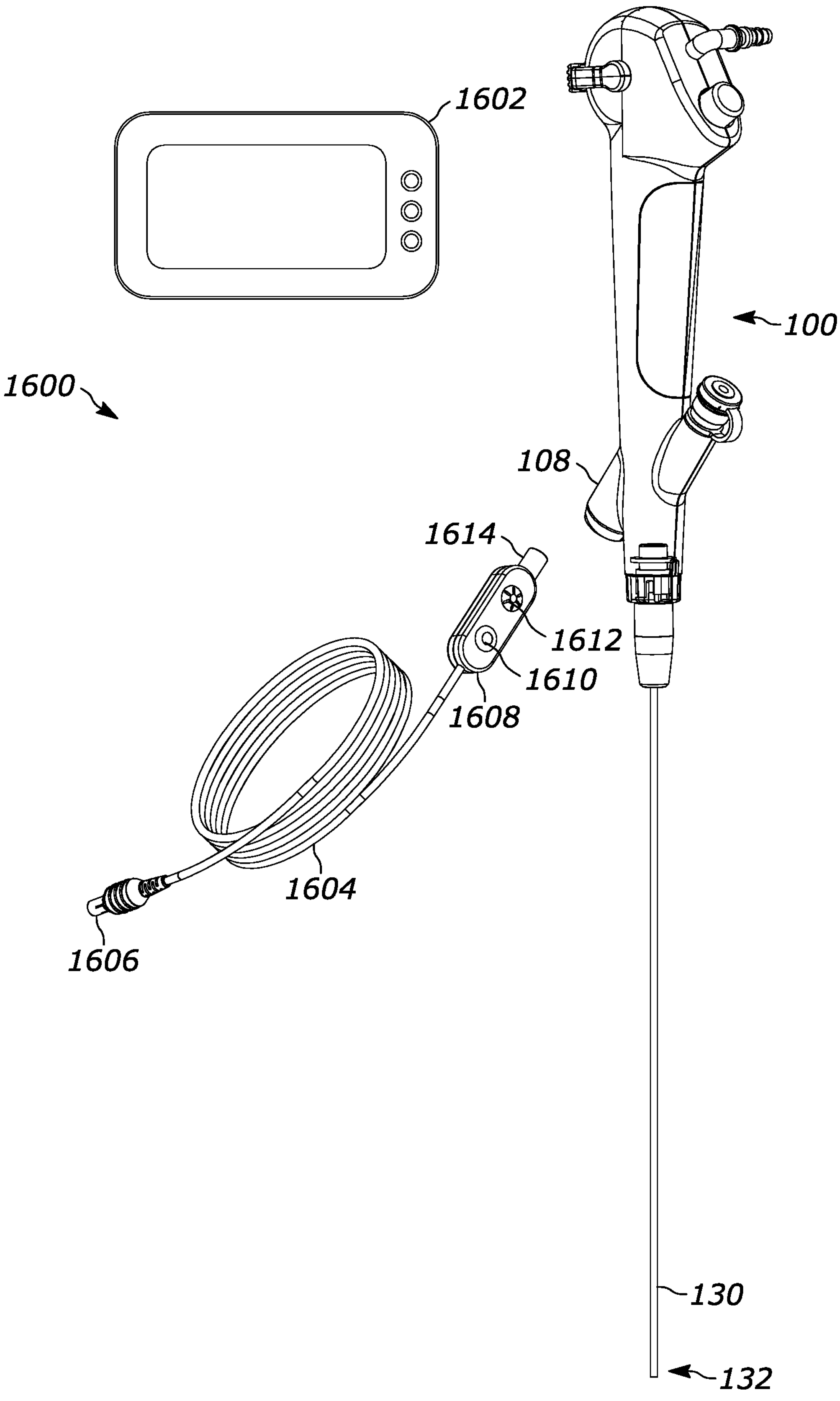
FIG. 16 is a schematic illustration of an endoscope system in accordance with an embodiment of the instant disclosure.
Figure 17:
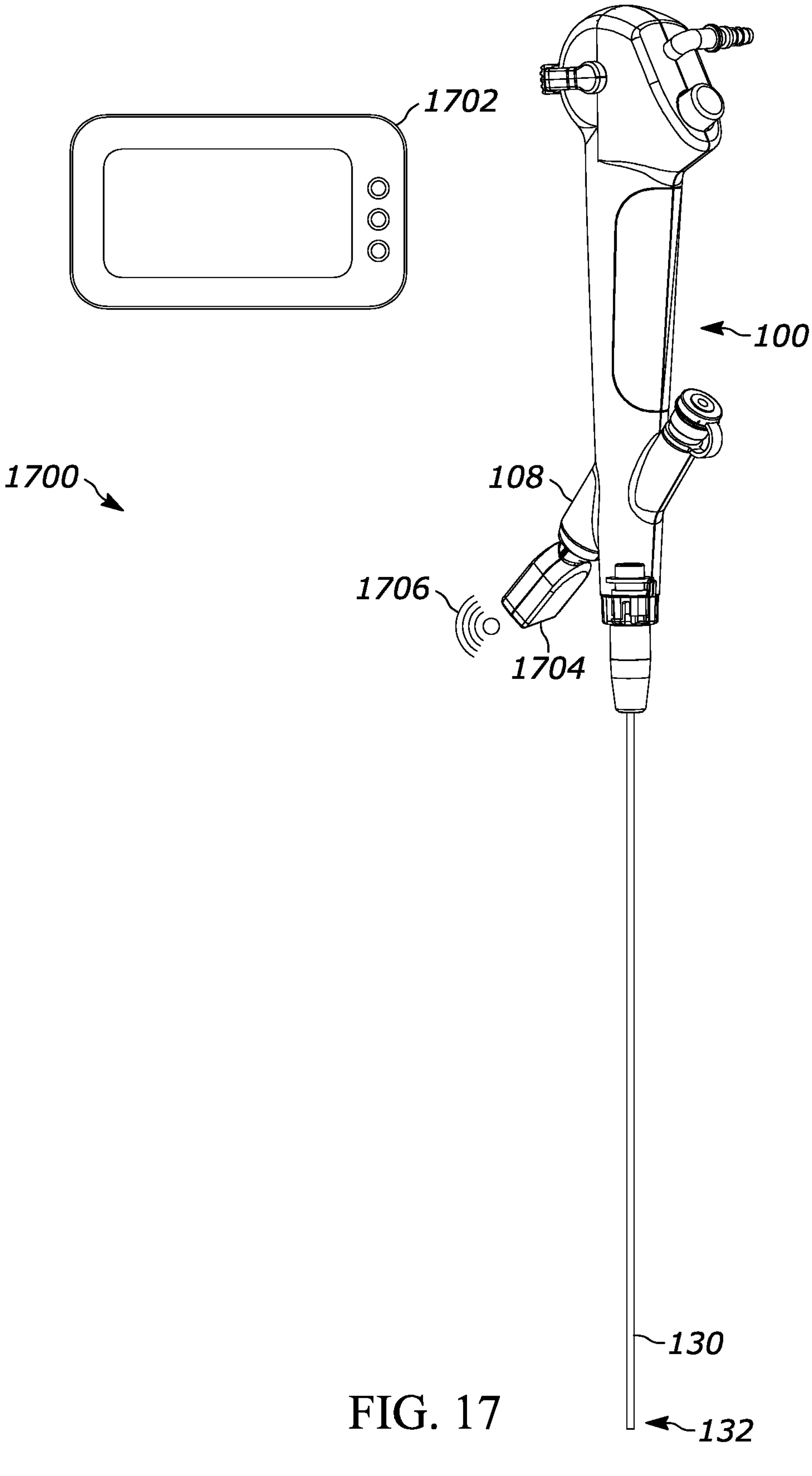
FIG. 17 is a schematic illustration of an endoscope system in accordance with an alternative embodiment of the instant disclosure.

Finally, FIGS. 16 and 17 illustrate steerable medical device (specifically, endoscope) systems in accordance with alternative embodiments. For example, FIG. 16 illustrates a system 1600 comprising a steerable medical device 100 as described above in combination with an external monitor 1602, as known in the art, suitable for viewing video images provided by a camera disposed at the distal tip 132. In this embodiment, the system 1600 further comprises a suitable video cable 1604 having a first connector 1606 for connection to the monitor 1602 and a second connector 1614 for mating with the video connector 211 accessed via the video port 108. As further shown, an inline controller 1608 comprising various control elements 1610, 1612 suitable to control the image quality of the camera (e.g., zoom or focus features, color contrast, lighting level controls, etc.) and/or to initiate recording of such images may be provided. Suitable video cables 1604 for this purpose will be known to those skilled in the art. FIG. 17 illustrates an alternative system 1700 in which the video cable 1604 is replaced with a wireless adapter 1704 to wirelessly communicate 1706 with a wireless-capable external monitor 1702. In this case, the adapter 1704 (which may be battery powered) is configured to mate with the video connector 211 and communicate with the monitor 1702 using suitable wireless communication protocols known to those skilled in the art.

Though specific implementations have been described herein, those skilled in the art will appreciate the various alterations may be employed without departing from the scope of the instant disclosure. For example, though the first and second steering cams 222, 224 are illustrated as radially extending arms, the steering cams could equally be implemented using wheel shapes or other geometric shapes with suitable wire attachment features. Furthermore, though the embodiments illustrated in FIGS. 1-9 show a single control device 220 provided in the steerable medical device 100, it is understood that this is not a requirement or limitation. That is, as known in the art, the steering wires 226, 232 provide the ability to deflect the distal tip 132 in opposite directions within a given plane (e.g., "N-S" using compass notation). However, by providing a second, substantially identical control device in the steerable medical device 100, but having steering wires configured to provide opposing deflections of the distal tip 132 in another plane different from the first control plane (preferably substantially orthogonal thereto, e.g., "E-W" using compass notation), it is possible to provide a user with even greater control capability. Additionally, as described above, the rotary knob assembly 120 included a detent 1404/recess 1118 combination respectively deployed within the housing 104 and knob 122. However, it is understood that the detent 1404 and recess 1118 could be opposite deployed, i.e., with a detent formed on the knob 122 and a recess formed in the housing 104. Further still, although a single detent 1404/recess 1118 combination has been described above, it is understood that multiple such combinations could be provided. For example, aside from having the detent 1404/recess 1118 combination defining the zero-rotation position, additional combinations of detent and recesses could be deployed at multiple different angular rotations to provide additional rotation position feedback, e.g., at 45° away from the zero-position indication in either direction.

What is claimed is:

1. A steerable medical device, comprising:
a housing;
an insertion tube;
a rotary knob assembly rotatably mounted on and extending out of the housing and affixed to the insertion tube, the rotary knob assembly comprising:
a bushing configured for rotatable mounting about a longitudinal axis of the housing;
a user-controllable knob having a longitudinally-extending tubular section, the knob affixed to the bushing such that the bushing rotates in unison with the knob and tubular section about the longitudinal axis; and
an endotracheal tube retainer affixed to the knob such that the knob rotates in unison with the tube retainer, wherein the tube retainer is fabricated from an elastomer material and an outer surface of the tube retainer is configured for frictional engagement with an inner surface of a tube connector of an endotracheal tube, wherein a longitudinally-extending channel is formed in the endotracheal tube retainer and defines a tube retainer sidewall, wherein at least one longitudinally extending slot is formed in the tube retainer sidewall, and wherein at least one shoulder is formed on an inner surface of the tube retainer sidewall and configured to engage radially-extending barbs formed on the tubular section.

2. The steerable medical device of claim 1, wherein the bushing comprises a radially extending flange configured for engagement with an annular channel formed in the housing.

3. The steerable medical device of claim 1, wherein the housing and knob respectively comprise at least one detent and at least one recess, or vice versa, configured for mutual engagement at least one defined-rotation position of the knob relative to the housing.

4. The steerable medical device of claim 1, wherein the housing comprises a housing stop surface and the knob comprises a knob stop surface and wherein the housing stop surface and the knob stop surface are configured to limit rotation of the knob when the housing stop surface contacts the knob stop surface.

5. The steerable medical device of claim 4, wherein the housing stop surface and the knob stop surface are configured to permit no more than 90° of rotation of the knob away from a zero-rotation position of the knob relative to the housing.

6. The steerable medical device of claim 1, wherein the tube retainer sidewall comprises at least one outer surface taper angle.

7. The steerable medical device of claim 6, wherein the tube retainer sidewall comprises two outer surface taper angles different from each other.

8. The steerable medical device of claim 1, further comprising:

first and second steering wires extending through the housing and the insertion tube toward a distal end of the insertion tube; and a control device supported by the housing and comprising:

a steering shaft rotatable about a longitudinal axis thereof and having at least one end configured to extend out of at least one opening formed in the housing;

a first steering cam affixed to the steering shaft such that the steering shaft rotates in unison with the first steering cam about the longitudinal axis of the steering shaft, the first steering cam further comprising a first attachment portion for attachment of the first steering wire;

a second steering cam mounted on the steering shaft and freely rotatable about the longitudinal axis of the steering shaft independent of the steering shaft, the second steering cam further comprising a second attachment portion for attachment of the second steering wire;

a latch assembly, operatively connected to the first steering cam and the second steering cam, operable in an inactive configuration in which the first and second steering cams are positioned such that the first and second steering wires are maintained in an un-tensioned state, and operable in an active configuration in which the first and second steering cams are positioned such that the first and second steering wires are maintained in a tensioned state; and a user-controllable lever disposed outside the housing and affixed to the at least one end of the steering shaft such that the steering shaft rotates in unison with the lever.

9. The steerable medical device of claim 8, wherein the first steering cam comprises a first facing surface and the second steering cam comprise a second facing surface configured to be opposite the first facing surface, and wherein the latch assembly further comprises:

at least one inactive notch and at least one active notch formed on the first facing surface;

at least one projection formed on the second facing surface, wherein, in the inactive configuration, alignment of the at least one projection with the at least one inactive notch positions the first and second steering cams such that the first and second steering wires are maintained in the un-tensioned state, and wherein, in the active configuration, alignment of the at least one projection with the at least one active notch positions the first and second steering cams such that the first and second steering wires are maintained in a tensioned state.

10. The steerable medical device of claim 9, further comprising:

a biasing element configured to bias the second facing surface into contact with the first facing surface.

11. The steerable medical device of claim 10, wherein the biasing element is a spring deployed about the steering shaft.

12. The steerable medical device of claim 9, wherein a depth of the at least one inactive notch is less than a depth of the at least one active notch.

13. The steerable medical device of claim 9, wherein a slope of a first sidewall of the at least one inactive notch is less than a slope of sidewalls of the at least one active notch.

* * * * *